(12) United States Patent
Bulu

(10) Patent No.: US 12,087,413 B2
(45) Date of Patent: Sep. 10, 2024

(54) METHOD, APPARATUS AND COMPUTER PROGRAM PRODUCT FOR GRAPH-BASED ENCODING OF NATURAL LANGUAGE DATA OBJECTS

(71) Applicant: UnitedHealth Group Incorporated, Minnetonka, MN (US)

(72) Inventor: Irfan Bulu, Sartell, MN (US)

(73) Assignee: UNITEDHEALTH GROUP INCORPORATED, Minnetonka, MN (US)

( * ) Notice: Subject to any disclaimer, the term of this patent is extended or adjusted under 35 U.S.C. 154(b) by 396 days.

(21) Appl. No.: 17/448,292

(22) Filed: Sep. 21, 2021

(65) Prior Publication Data

US 2023/0085697 A1  Mar. 23, 2023

(51) Int. Cl.
*G16H 10/60* (2018.01)
*G06F 16/33* (2019.01)
(Continued)

(52) U.S. Cl.
CPC ......... *G16H 10/60* (2018.01); *G06F 16/3344* (2019.01); *G06F 40/279* (2020.01); *G06T 11/206* (2013.01)

(58) Field of Classification Search
CPC ........ G16H 10/60; G16H 50/70; G16H 50/20; G06F 16/3344; G06F 40/279; G06T 11/206
(Continued)

(56) References Cited

U.S. PATENT DOCUMENTS

| 7,383,169 B1 | 6/2008 | Vanderwende et al. |
| 9,400,778 B2 | 7/2016 | Ramani et al. |

(Continued)

FOREIGN PATENT DOCUMENTS

| WO | 2021/002800 A1 | 1/2021 | |
| WO | WO-2021195130 A1 * | 9/2021 | ......... G06F 16/2237 |

OTHER PUBLICATIONS

Yao et al., "KG-BERT: BERT for Knowledge Graph Completion," arXiv Preprint, arXiv:1909.031932v2 [cs.CL], Sep. 11, 2019, 8 pages (Year: 2019).*

(Continued)

*Primary Examiner* — Joy Chng
(74) *Attorney, Agent, or Firm* — Alston & Bird LLP

(57) ABSTRACT

Methods, apparatuses, systems, computing devices, and/or the like are provided. An example method may include retrieving a plurality of natural language data objects from a database; determining, based at least in part on the plurality of natural language data objects and by utilizing an entity extraction machine learning model, a plurality of entity identifiers for the plurality of natural language data objects; determining, based at least in part on the plurality of entity identifiers and by utilizing the entity extraction machine learning model, one or more entity relationship identifiers for the plurality of natural language data objects; generating, based at least in part on the plurality of entity identifiers and the one or more entity relationship identifiers, a graph-based data object for the plurality of natural language data objects; and performing one or more prediction based actions based at least in part on the graph-based data object.

20 Claims, 14 Drawing Sheets

(51) Int. Cl.
*G06F 40/279* (2020.01)
*G06T 11/20* (2006.01)

(58) Field of Classification Search
USPC .......................................................... 705/2–3
See application file for complete search history.

(56) References Cited

U.S. PATENT DOCUMENTS

| | | | |
|---|---|---|---|
| 9,904,668 | B2 | 2/2018 | Bruno et al. |
| 10,649,985 | B1 | 5/2020 | Cornell, Jr. et al. |
| 11,030,691 | B2 | 6/2021 | Parmar et al. |
| 11,151,982 | B2* | 10/2021 | Tomkins .................. G06N 3/04 |
| 2017/0308521 | A1* | 10/2017 | Bruno .................... G06F 40/205 |
| 2018/0174255 | A1 | 6/2018 | Hunn et al. |
| 2018/0239959 | A1 | 8/2018 | Bui et al. |
| 2018/0315141 | A1 | 11/2018 | Hunn et al. |
| 2021/0294828 | A1* | 9/2021 | Tomkins ............. G06F 16/3329 |
| 2022/0277315 | A1* | 9/2022 | Mittal ................... G06F 16/951 |

OTHER PUBLICATIONS

Geer, David. "How Smart Contracts Can Create a Competitive Edge," Journal of Accountancy, Aug. 6, 2018, (4 pages), Available Online <URL: https://www.journalofaccountancy.com/newsletters/2018/aug/smart-contracts-competitive-edge.html>.

Kanowitz, Stephanie. "How the Army's DORA Bot Cuts Manual Work for Contracting Professionals," Government Computer News (GCN), Oct. 28, 2020, (3 pages), Available Online <URL: https://gcn.com/2020/10/how-the-armys-dora-bot-cuts-manual-work-for-contracting-professionals/315706/>.

Koniaris, Marios et al. "Network Analysis in the Legal Domain: A Complex Model for European Union Legal Sources," arXiv Preprint, arXiv:1501.05237v3 [cs.SI], Feb. 9, 2017, (29 pages), Available Online <URL: https://arxiv.org/pdf/1501.05237.pdf>.

Schneider, Julian Moreno et al. "Curation Technologies for the Construction and Utilisation of Legal Knowledge Graphs," In Proceedings of the LREC 2018 Workshop on Language Resources and Technologies for the Legal Knowledge Graph, May 12, 2018 pp. 23-29.

SNOMED International Determine Global Standards for Health Terms, an Essential Part of Improving the Health of Humankind, SNOMED International, (1 page), [Retrieved from the Internet Dec. 30, 2021) <URL: https://www.snomed.org/>.

Yao, Liang et al. "KG-BERT: BERT for Knowledge Graph Completion," arXiv Preprint, arXiv:1909.031932v2 [cs.CL], Sep. 11, 2019, (8 pages).

* cited by examiner

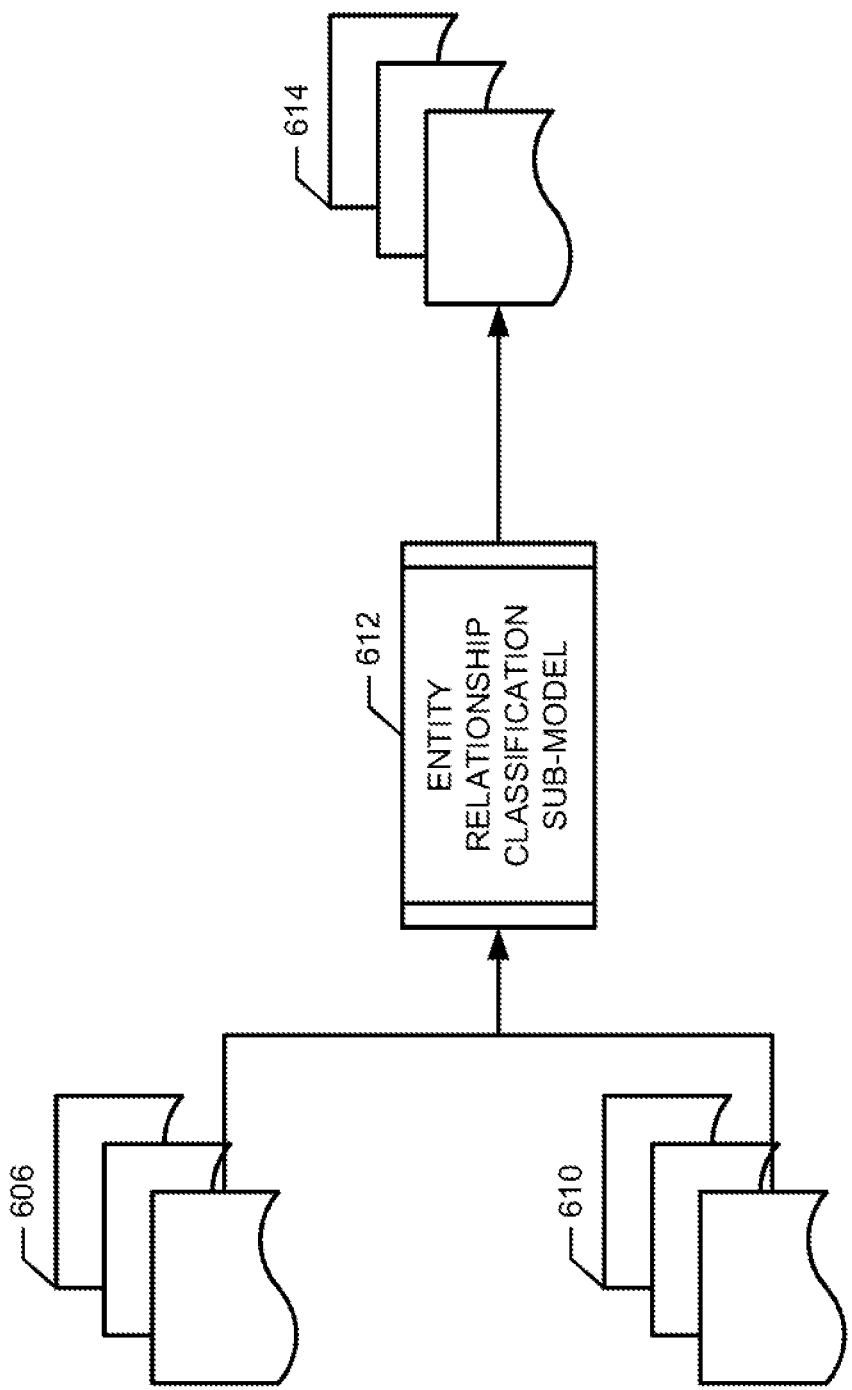

METHOD, APPARATUS AND COMPUTER PROGRAM PRODUCT FOR GRAPH-BASED ENCODING OF NATURAL LANGUAGE DATA OBJECTS

TECHNOLOGICAL FIELD

Embodiments of the present disclosure relate generally to improving computer and data system functionalities, such as, but not limited to, functionalities of natural language processing and machine learning systems. For example, various embodiments of the present disclosure may programmatically generate a graph-based data object based at least in part on a plurality of natural language data objects and perform one or more prediction-based actions based at least in part on the graph-based data object.

BACKGROUND

Natural language processing and machine learning systems have great potential for providing various technical advancement and technical benefits not only in the field of computer science, but also in other associated technical fields and applications. Applicant has identified many technical challenges, deficiencies and problems associated with natural language processing and machine learning systems and methods.

BRIEF SUMMARY

In general, embodiments of the present disclosure provide methods, apparatuses, systems, computing devices, computing entities, and/or the like.

In accordance with various embodiments of the present disclosure, an apparatus is provided. The apparatus may comprise at least one processor and at least one non-transitory memory comprising a computer program code. The at least one non-transitory memory and the computer program code may be configured to, with the at least one processor, cause the apparatus to retrieve a plurality of natural language data objects from a database; determine, based at least in part on the plurality of natural language data objects and by utilizing an entity extraction machine learning model, a plurality of entity identifiers for the plurality of natural language data objects, wherein: (i) the entity extraction machine learning model comprises an encoder sub-model and an entity classification sub-model, (ii) the encoder sub-model is configured to generate a plurality of text embeddings based at least in part on the plurality of natural language data objects, (iii) the entity classification sub-model is configured to determine an entity classification for each text embedding, and (iv) the plurality of entity identifiers are determined based at least in part on each entity classification; determine, based at least in part on the plurality of entity identifiers and by utilizing the entity extraction machine learning model, one or more entity relationship identifiers for the plurality of natural language data objects, wherein: (i) the entity extraction machine learning model comprises an entity relationship classification sub-model, (ii) the entity relationship classification sub-model is configured to determine an entity relationship classification for each entity pair from the plurality of entity identifiers based at least in part on a subset of the plurality of text embeddings that corresponds to the entity pair, and (iii) the one or more entity relationship identifiers are determined based at least in part on each entity relationship classification; generate, based at least in part on the plurality of entity identifiers and the one or more entity relationship identifiers, a graph-based data object for the plurality of natural language data objects; and perform one or more prediction-based actions based at least in part on the graph-based data object.

In some embodiments, the encoder sub-model is associated with a multi-headed attention mechanism.

In some embodiments, the encoder sub-model comprises a Bidirectional Encoder Representations from Transformers (BERT) model.

In some embodiments, when generating the graph-based data object, the at least one non-transitory memory and the computer program code are configured to, with the at least one processor, cause the apparatus to: generate a plurality of nodes of the graph-based data object based at least in part on the plurality of entity identifiers; and generate a plurality of edges of the graph-based data object based at least in part on the one or more entity relationship identifiers.

In some embodiments, the plurality of natural language data objects comprises at least one textual contract data object and at least one medical record data object.

In some embodiments, when generating the graph-based data object, the at least one non-transitory memory and the computer program code are configured to, with the at least one processor, cause the apparatus to: in response to determining that the at least one textual contract data object and the at least one medical record data object are associated with a first patient entity identifier of the plurality of entity identifiers, generate a patient entity node; generate, based at least in part on the at least one medical record data object, at least one symptom node and a first edge connecting the at least one symptom node to the patient entity node; and generate, based at least in part on the at least one textual contract data object, at least one procedure node and a second edge connecting the at least one procedure node to the patent entity node.

In some embodiments, the at least one procedure node is associated with at least one International Classification of Diseases (ICD) code.

In some embodiments, the graph-based data object comprises a plurality of nodes and a plurality of edges connecting the plurality of nodes. In some embodiments, each of the plurality of nodes corresponds to an entity associated with the plurality of natural language data objects. In some embodiments, each of the plurality of edges corresponds to a relationship between entities associated with the plurality of natural language data objects.

In some embodiments, the plurality of nodes is associated with a plurality of node types. In some embodiments, the plurality of edges is associated with a plurality of edge types that is determined based at least in part on the plurality anode types.

In some embodiments, when performing the one or more prediction-based actions, the at least one non-transitory memory and the computer program code are configured to, with the at least one processor, cause the apparatus to: receive, from a client computing device, a data prediction request associated with at least one entity identifier of the plurality of entity identifiers; in response to receiving the data prediction request, identify, based at least in part on the at least one entity identifier, a related sub-graph of the graph-based data object that corresponds to the at least one entity identifier; generate, based at least in part on the related sub-graph, at least one prediction data object using a data prediction machine learning model; and transmit the at least one prediction data object to the client computing device.

In some embodiments, when identifying the related sub-graph of the graph-based data object that corresponds to the at least one entity identifier, the at least one non-transitory memory and the computer program code are configured to, with the at least one processor, cause the apparatus to: determine at least a first node from a plurality of nodes of the graph-based data object that is associated with the at least one entity identifier; and determine at least a first edge from a plurality of edges of the graph-based data object that connects the first node to at least a second node.

In some embodiments, when performing the one or more prediction-based actions, the at least one non-transitory memory and the computer program code are configured to, with the at least one processor, cause the apparatus to: generate the at least one prediction data object based at least in part on the first node, the first edge, and the second node using the data prediction machine learning model.

In some embodiments, the at least one non-transitory memory and the computer program code are configured to, with the at least one processor, cause the apparatus to: train the data prediction machine learning model using a training data set, wherein the training data set comprises a plurality of historical data prediction requests that corresponds to a plurality of historical response data objects; and subsequent to training the data prediction machine learning model, generate the at least one prediction data object based at least in part on the data prediction request and the graph-based data object.

In some embodiments, the data prediction request is associated with a preauthorization request and comprises a procedure identifier, a patient entity identifier, a healthcare provider entity identifier, and a health insurance provider entity identifier.

In some embodiments, when generating the at least one prediction data object, the at least one non-transitory memory and the computer program code are configured to, with the at least one processor, cause the apparatus to: identify, from a plurality of nodes of the graph-based data object, a patient entity node associated with the patient entity identifier; identify, from the plurality of nodes of the graph-based data object, a healthcare provider entity node associated with the healthcare, provider entity identifier; identify, from the plurality of nodes of the graph-based data object, a procedure node associated with the procedure identifier; and calculate, based at least in part on the data prediction machine learning model, (i) a prediction data object indicating a predicted probability of at least one edge connecting the procedure node to the patient entity node and to the healthcare provider entity node and (ii) a prediction confidence score associated with the prediction data object. In some embodiments, the data prediction machine learning model is an unsupervised machine learning model.

In some embodiments, the at least one non-transitory memory and the computer program code are configured to, with the at least one processor, cause the apparatus to: determine whether the prediction confidence score satisfies a data prediction threshold.

In some embodiments, the at least one non-transitory memory and the computer program code are configured to, with the at least one processor, cause the apparatus to: in response to determining that the prediction confidence score satisfies the data prediction threshold, generate at least one recommendation data object based at least in part on the at least one prediction data object.

In some embodiments, the at least one non-transitory memory and the computer program code are configured to, with the at least one processor, cause the apparatus to: in response to determining that the prediction confidence score does not satisfy the data prediction threshold, transmit a data prediction review request to the client computing device.

In accordance with various embodiments of the present disclosure, a computer-implemented method is provided. The computer-implemented method may comprise retrieving, using a processor, a plurality of natural language data objects from a database; determining, using the processor and based at least in part on the plurality of natural language data objects and by utilizing an entity extraction machine learning model, a plurality of entity identifiers for the plurality of natural language data objects, wherein: (i) the entity extraction machine learning, model comprises an encoder sub-model and an entity classification sub-model, (ii) the encoder sub-model is configured to generate a plurality of text embeddings based at least in part on the plurality of natural language data objects, (iii) the entity classification sub-model is configured to determine an entity classification for each text embedding, and (iv) the plurality of entity identifiers are determined based at least in part on each entity classification; determining, using the processor and based at least in part on the plurality of entity identifiers and by utilizing the entity extraction machine learning model, one or more entity relationship identifiers for the plurality of natural language data objects, wherein: (i) the entity extraction machine learning model comprises an entity relationship classification sub-model, (ii) the entity relationship classification sub-model is configured to determine an entity relationship classification for each entity pair from the plurality of entity identifiers based at least in part on a subset of the plurality of text embeddings that corresponds to the entity pair, and (iii) the one or more entity relationship identifiers are determined based at least in part on each entity relationship classification; generating, using the processor and based at least in part on the plurality of entity identifiers and the one or more entity relationship identifiers, a graph-based data object for the plurality of natural language data objects; and performing, using the processor, one or more prediction-based actions based at least in part on the graph-based data object.

In accordance with various embodiments of the present disclosure, a computer program product is provided. The computer program product may comprise at least one non-transitory computer-readable storage medium having computer-readable program code portions stored therein. The computer-readable program code portions may comprise an executable portion configured to retrieve a plurality of natural language data objects from a database; determine, based at least in part on the plurality of natural language data objects and by utilizing an entity extraction machine learning model, a plurality of entity identifiers for the plurality of natural language data objects, wherein: (i) the entity extraction machine learning model comprises an encoder sub-model and an entity classification sub-model, (ii) the encoder sub-model is configured to generate a plurality of text embeddings based at least in part on the plurality of natural language data objects, (iii) the entity classification sub-model is configured to determine an entity classification for each text embedding, and (iv) the plurality of entity identifiers are determined based at least in part on each entity classification; determine, based at least in part on the plurality of entity identifiers and by utilizing the entity extraction machine learning model, one or more entity relationship identifiers for the plurality of natural language data objects, wherein: (i) the entity extraction machine learning model comprises an entity relationship classification sub-model, (ii) the entity relationship classification sub-model is configured to determine an entity relationship classification for each entity pair from the plurality of entity identifiers based at least in part on a subset of the plurality of text embeddings that corresponds to the entity pair, and (iii) the one or more entity relationship identifiers are determined based at least in part on each entity relationship classification; generate, based at least in part on the plurality of entity identifiers and the one or more entity relationship identifiers, a graph-based data object for the plurality of natural language data objects; and perform one or more prediction-based actions based at least in part on the graph-based data object.

The above summary is provided merely for purposes of summarizing some example embodiments to provide a basic understanding of some aspects of the disclosure. Accordingly, it will be appreciated that the above-described embodiments are merely examples. It will be appreciated that the scope of the disclosure encompasses many potential embodiments in addition to those here summarized, some of which will be further described below.

BRIEF DESCRIPTION OF THE SEVERAL VIEWS OF THE DRAWING(S)

Having thus described the disclosure in general terms, reference will now be made to the accompanying drawings, which are not necessarily drawn to scale, and wherein:

Figure 3:
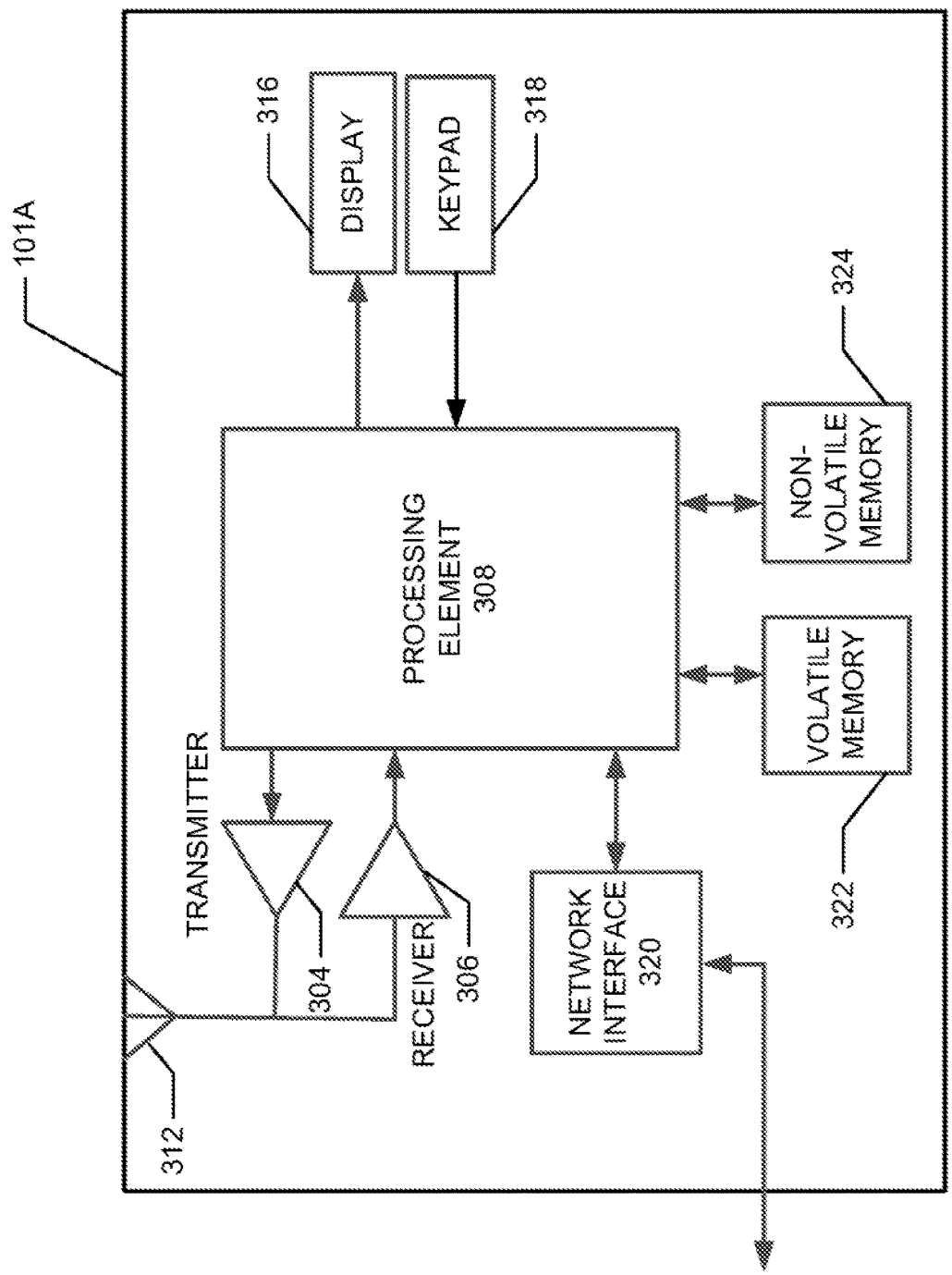

FIG. 3 is a schematic representation of an example client computing entity in accordance with various embodiments of the present disclosure; and FIGS. 4, 5, 6A, 6B, 7, 8, 9, 10, 11, 12, and 13 provide example flowcharts and diagrams illustrating example steps, processes, procedures, and/or operations associated with an example natural language processing and machine learning platform/system in accordance with various embodiments of the present disclosure.

DETAILED DESCRIPTION OF SOME EXAMPLE EMBODIMENTS

Various embodiments of the present disclosure now will be described more fully hereinafter with reference to the accompanying drawings, in which some, but not all embodiments of the disclosure are shown. Indeed, this disclosure may be embodied in many different forms and should not be construed as limited to the embodiments set forth herein; rather, these embodiments are provided so that this disclosure will satisfy applicable legal requirements. The term "or" (also designated as "/") is used herein in both the alternative and conjunctive sense, unless otherwise indicated. The terms "illustrative" and "exemplary" are used to be examples with no indication of quality level. Like numbers may refer to like elements throughout. The phrases "in one embodiment," "according to one embodiment," and/or the like generally mean that the particular feature, structure, or characteristic following the phrase may be included in at least one embodiment of the present disclosure and may be included in more than one embodiment of the present disclosure (importantly, such phrases do not necessarily may refer to the same embodiment).

I. Computer Program Products, Methods, and Computing Entities

Embodiments of the present disclosure may be implemented as computer program products that comprise articles of manufacture. Such computer program products may include one or more software components including, for example, applications, software objects, methods, data structures, and/or the like. A software component may be coded in any of a variety of programming languages. An illustrative programming language may be a lower-level programming language such as an assembly language associated with a particular hardware architecture and/or operating system platform/system. A software component comprising assembly language instructions may require conversion into executable machine code by an assembler prior to execution by the hardware architecture and/or platform/system. Another example programming language may be a higher-level programming language that may be portable across multiple architectures. A software component comprising higher-level programming language instructions may require conversion to an intermediate representation by an interpreter or a compiler prior to execution.

Other examples of programming languages include, but are not limited to, a macro language, a shell or command language, a job control language, a script language, a database query or search language, and/or a report writing language. In one or more example embodiments, a software component comprising instructions in one of the foregoing examples of programming languages may be executed directly by an operating system or other software component without having to be first transformed into another form. A software component may be stored as a file or other data storage construct. Software components of a similar type or functionally related may be stored together such as, for example, in a particular directory, folder, or library. Software components may be static (e.g., pre-established or fixed) or dynamic (e.g., created or modified at the time of execution).

Additionally, or alternatively, embodiments of the present disclosure may be implemented as a non-transitory computer-readable storage medium storing applications, programs, program modules, scripts, source code, program code, object code, byte code, compiled code, interpreted code, machine code, executable instructions, and/or the like (also referred to herein as executable instructions, instructions for execution, computer program products, program code, and/or similar terms used herein interchangeably). Such non-transitory computer-readable storage media may include all computer-readable media (including volatile and non-volatile media).

In one embodiment, a non-volatile computer-readable storage medium may include a floppy disk, flexible disk, hard disk, solid-state storage (SSS) (e.g., a solid-state drive (SSD), solid state card (SSC), solid state module (SSM), enterprise flash drive, magnetic tape, or any other non-transitory magnetic medium, and/or the like. A non-volatile computer-readable storage medium may also include a punch card, paper tape, optical mark sheet (or any other physical medium with patterns of holes or other optically recognizable indicia), compact disc read only memory (CD-ROM), compact disc-rewritable (CD-RW), digital versatile disc (DVD), Blu-ray disc (BD), any other non-transitory optical medium, and/or the like. Such a non-volatile computer-readable storage medium may also include read-only memory (ROM), programmable read-only memory (PROM), erasable programmable read-only memory (EPROM), electrically erasable programmable read-only memory (EEPROM), flash memory (e.g., Serial, NAND, NOR, and/or the like) multimedia memory cards (MMC), secure digital (SD) memory cards, SmartMedia cards, CompactFlash (CF) cards, Memory Sticks, and/or the like. Further, a non-volatile computer-readable storage medium may also include conductive-bridging random access memory (CBRAM), phase-change random access memory (PRAM), ferroelectric random-access memory (FeRAM), non-volatile random-access memory (NVRAM), magnetoresistive random-access memory (MRAM), resistive random-access memory (RRAM), Silicon-Oxide-Nitride-Oxide-Silicon memory (SONOS), floating junction gate random access memory (FJG RAM), Millipede memory, racetrack memory, and/or the like.

In one embodiment, a volatile computer-readable storage medium may include random access memory (RAM), dynamic random access memory (DRAM), static random access memory (SRAM), fast page mode dynamic random access memory (FPM DRAM), extended data-out dynamic random access memory (EDO DRAM), synchronous dynamic random access memory (SDRAM), double data rate synchronous dynamic random access memory (DDR SDRAM), double data rate type two synchronous dynamic random access memory (DDR2 SDRAM), double data rate type three synchronous dynamic random access memory (DDR3 SDRAM), Rambus dynamic random access memory (RDRAM), Twin Transistor RAM (TTRAM), Thyristor RAM (T-RAM), Zero-capacitor (Z-RAM), Rambus in-line memory module (RIMM), dual in-line memory module (DIMM) single in-line memory module (SIMM), video random access memory (VRAM), cache memory (including various levels), flash memory, register memory, and/or the like. It will be appreciated that where embodiments are described to use a computer-readable storage medium, other types of computer-readable storage media may be substituted for or used in addition to the computer-readable storage media described above.

As should be appreciated, various embodiments of the present disclosure may also be implemented as methods, apparatuses, systems, computing devices, computing entities, and/or the like. As such, embodiments of the present disclosure may take the form of a data structure, apparatus, system, computing device, computing entity, and/or the like executing instructions stored on a computer-readable storage medium to perform certain steps or operations. Thus, embodiments of the present disclosure may also take the form of an entirely hardware embodiment, an entirely computer program product embodiment, and/or an embodiment that comprises combination of computer program products and hardware performing certain steps or operations.

Embodiments of the present disclosure are described below with reference to block diagrams and flowchart illustrations. Thus, it should be understood that each block of the block diagrams and flowchart illustrations may be implemented in the form of a computer program product, an entirely hardware embodiment, a combination of hardware and computer program products, and/or apparatus, systems, computing devices, computing entities, and/or the like carrying out instructions, operations, steps, and similar words used interchangeably (e.g., the executable instructions, instructions for execution, program code, and/or the like) on a computer-readable storage medium for execution. For example, retrieval, loading, and execution of code may be performed sequentially such that one instruction is retrieved, loaded, and executed at a time. In some exemplary embodiments, retrieval, loading, and/or execution may be performed parallel such that multiple instructions are retrieved, loaded, and/or executed together. Thus, such embodiments can produce specifically-configured machines performing the steps or operations specified in the block diagrams and flowchart illustrations. Accordingly, the block diagrams and flowchart illustrations support various combinations of embodiments for performing the specified instructions, operations, or steps.

II. Exemplary System Architecture

Figure 1:
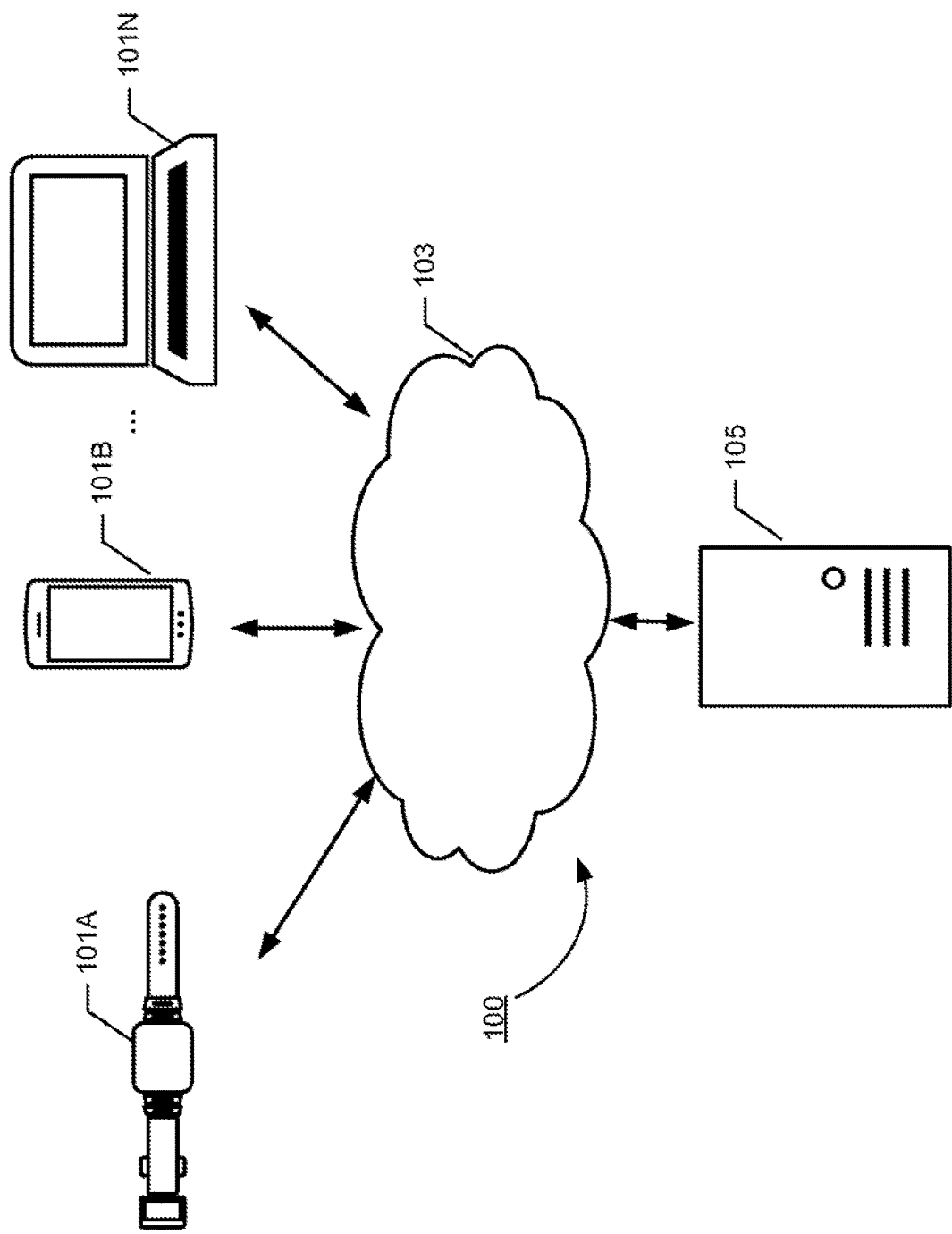
FIG. 1 is a diagram of an example natural language processing and machine learning platform/system that can be used in accordance with various embodiments of the present disclosure.

FIG. 1 provides an illustration of a natural language processing and machine learning platform/system 100 that can be used in conjunction with various embodiments of the present disclosure. As shown in FIG. 1, the natural language processing and machine learning platform/system 100 may comprise one or more data object computing entities 105, one or more client computing entities 101A, 101B . . . 101N, and one or more networks 103. Each of the components of the natural language processing and machine learning platform/system 100 may be in electronic communication with, for example, one another over the same or different wireless or wired networks 103 including, for example, a wired or wireless Personal Area Network (PAN), Local Area Network (LAN), Metropolitan Area Network (MAN), Wide Area Network (WAN), and/or the like. Additionally, while FIG. 1 illustrates certain system entities as separate, standalone entities, the various embodiments are not limited to this particular architecture.

a. Exemplary Data Object Computing Entity

Figure 2:
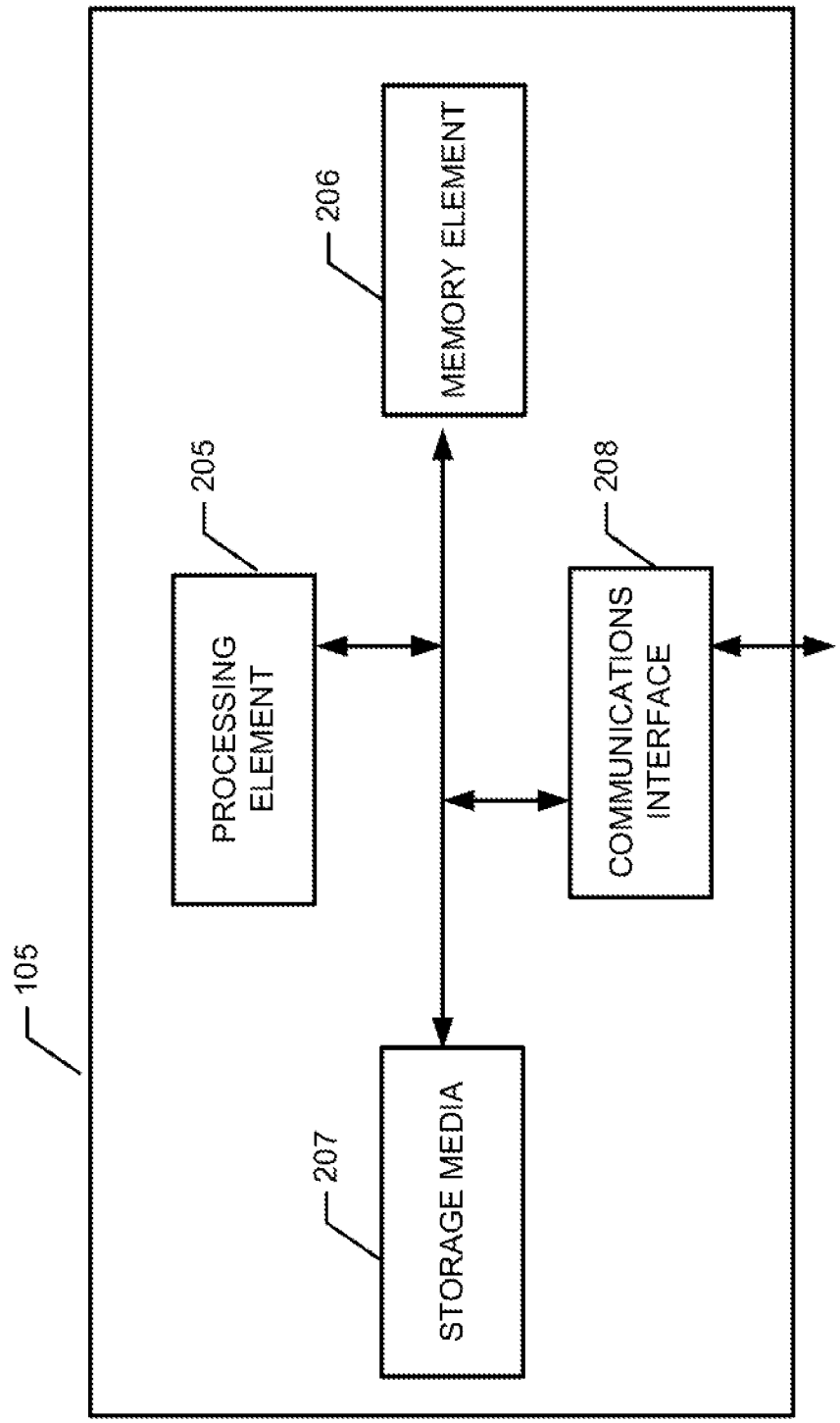
FIG. 2 is a schematic representation of an example data object computing entity in accordance with various embodiments of the present disclosure.

FIG. 2 provides a schematic of a data object computing entity 105 according to one embodiment of the present disclosure. In general, the terms computing entity, entity, device, system, and/or similar words used herein interchangeably may refer to, for example, one or more computers, computing entities, desktop computers, mobile phones, tablets, phablets, notebooks, laptops, distributed systems, items/devices, terminals, servers or server networks, blades, gateways, switches, processing devices, processing entities, set-top boxes, relays, routers, network access points, base stations, the like, and/or any combination of devices or entities adapted to perform the functions, operations, and/or processes described herein. Such functions, operations, and/or processes may include, for example, transmitting, receiving, operating on, processing, displaying, storing, determining, creating/generating, monitoring, evaluating, comparing, and/or similar terms used herein. In one embodiment, these functions, operations, and/or processes can be performed on data, content, information, and/or similar terms used herein.

As indicated, in one embodiment, the data object computing entity 105 may also include one or more network and/or communications interface 208 for communicating with various computing entities, such as by communicating data, content, information, and/or similar terms used herein that can be transmitted, received, operated on, processed, displayed, stored, and/or the like. For instance, the data object computing entity 105 may communicate with other data object computing entities 105, one or more client computing entities 101A-101N, and/or the like.

As shown in FIG. 2, in one embodiment, the data object computing entity 105 may include or be in communication with one or more processing elements (for example, processing element 205) (also referred to as processors, processing circuitry, and/or similar terms used herein interchangeably) that communicate with other elements within the data object computing entity 105 via a bus, for example, or network connection. As will be understood, the processing element 205 may be embodied in a number of different ways. For example, the processing element 205 may be embodied as one or more complex programmable logic devices (CPLDs), microprocessors, multi-core processors, coprocessing entities, application-specific instruction-set processors (ASICs), and/or controllers. Further, the processing element 205 may be embodied as one or more other processing devices or circuitry. The term circuitry may refer to an entirely hardware embodiment or a combination of hardware and computer program products. Thus, the processing element 205 may be embodied as integrated circuits, application specific integrated circuits (ASICs), field programmable gate arrays (FPGAs), programmable logic arrays (PLAs), hardware accelerators, other circuitry, and/or the like. As will therefore be understood, the processing element 205 may be configured for a particular use or configured to execute instructions stored in volatile or non-volatile media or otherwise accessible to the processing element 205. As such, whether configured by hardware or computer program products, or by a combination thereof, the processing element 205 may be capable of performing steps or operations according to embodiments of the present disclosure when configured accordingly.

In one embodiment, the data object computing entity 105 may further include or be in communication with volatile media (also referred to as volatile storage, memory, memory storage, memory circuitry and/or similar terms used herein interchangeably). In one embodiment, the volatile storage or memory may also include one or more memory element 206 as described above, such as RAM, DRAM, SRAM, FPM DRAM, EDO DRAM, SDRAM, DDR SDRAM, DDR2 SDRAM, DDR3 SDRAM, RDRAM, RIMM, DIMM, SIMM, VRAM, cache memory, register memory, and/or the like. As will be recognized, the volatile storage or memory element 206 may be used to store at least portions of the databases, database instances, database management system entities, data, applications, programs, program modules, scripts, source code, object code, byte code, compiled code, interpreted code, machine code, executable instructions, and/or the like being executed by, for example, the processing element 205 as shown in FIG. 2 and/or the processing element 308 as described in connection with FIG. 3. Thus, the databases, database instances, database management system entities, data, applications, programs, program modules, scripts, source code, object code, byte code, compiled code, interpreted code, machine code, executable instructions, and/or the like may be used to control certain aspects of the operation of the data object computing entity 105 with the assistance of the processing element 205 and operating system.

In one embodiment, the data object computing entity 105 may further include or be in communication with non-volatile media (also referred to as non-volatile storage, memory, memory storage, memory circuitry and/or similar terms used herein interchangeably). In one embodiment, the non-volatile storage or memory may include one or more non-volatile storage or storage media 207 as described above, such as hard disks, ROM, PROM, EPROM, EEPROM flash memory, MMCs, SD memory cards, Memory Sticks, CBRAM, PRAM, FeRAM, RRAM, SONOS, racetrack memory, and/or the like. As will be recognized, the non-volatile storage or storage media 207 may store databases, database instances, database management system entities, data, applications, programs, program modules, scripts, source code, object code, byte code, compiled code, interpreted code, machine code, executable instructions, and/or the like. The term database, database instance, database management system entity, and/or similar terms used herein interchangeably and in a general sense to may refer to a structured or unstructured collection of information/data that is stored in a computer-readable storage medium.

Storage media 207 may also be embodied as a data storage device or devices, as a separate database server or servers, or as a combination of data storage devices and separate database servers. Further, in some embodiments, storage media 207 may be embodied as a distributed repository such that some of the stored information/data is stored centrally in a location within the system and other information/data is stored in one or more remote locations. Alternatively, in some embodiments, the distributed repository may be distributed over a plurality of remote storage locations only. An example of the embodiments contemplated herein would include a cloud data storage system maintained by a third-party provider and where some or all of the information/data required for the operation of the recovery prediction system may be stored. Further, the information/data required for the operation of the recovery prediction system may also be partially stored in the cloud data storage system and partially stored in a locally maintained data storage system. More specifically, storage media 207 may encompass one or more data stores configured to store information/data usable in certain embodiments.

As indicated, in one embodiment, the data object computing entity 105 may also include one or more network and/or communications interface 208 for communicating with various computing entities, such as by communicating data, content, information, and/or similar terms used herein interchangeably that can be transmitted, received, operated on, processed, displayed, stored, and/or the like. For instance, the data object computing entity 105 may communicate with computing entities or communication interfaces of other data object computing entities 105, client computing entities 101A-101N, and/or the like.

As indicated, in one embodiment, the data object computing entity 105 may also include one or more network and/or communications interface 208 for communicating with various computing entities, such as by communicating data, content, information, and/or similar terms used herein interchangeably that can be transmitted, received, operated on, processed, displayed, stored, and/or the like. Such communication may be executed using a wired data transmission protocol, such as fiber distributed data interface (FDDI), digital subscriber line (DSL), Ethernet, asynchronous transfer mode (ATM), frame relay, data over cable service interface specification (DOCSIS), or any other wired transmission protocol. Similarly, the data object computing entity 105 may be configured to communicate via wireless external communication networks using any of a variety of protocols, such as general packet radio service (GPRS), Universal Mobile Telecommunications System (UMTS), Code Division Multiple Access 1900 (CDMA1900), CDMA1900 1X (1×RTT), Wideband Code Division Multiple Access (WCDMA), Global System for Mobile Communications (GSM), Enhanced Data rates for GSM Evolution (EDGE), Time Division-Synchronous Code Division Multiple Access (TD-SCDMA), Long Term Evolution (LTE), Evolved Universal Terrestrial Radio Access Network (E-UTRAN), Evolution-Data Optimized (EVDO), High Speed Packet Access (HSPA), High-Speed Downlink Packet Access (HSDPA), Institute of Electrical and Electronics Engineers (IEEE) 802.11 (Wi-Fi), Wi-Fi Direct, 802.16 (WiMAX), ultra-wideband (UWB), infrared (IR) protocols, near field communication (NFC) protocols, Wibree, Bluetooth protocols, wireless universal serial bus (USB) protocols, and/or any other wireless protocol. The data object computing entity 105 may use such protocols and standards to communicate using Border Gateway Protocol (BGP), Dynamic Host Configuration Protocol (DHCP), Domain Name System (DNS), File Transfer Protocol (FTP), Hypertext Transfer Protocol (HTTP), HTTP over TLS/SSL/Secure, Internet Message Access Protocol (IMAP), Network Time Protocol (NTP), Simple Mail Transfer Protocol (SMTP), Telnet, Transport Layer Security (TLS), Secure Sockets Layer (SSL), Internet Protocol (IP), Transmission Control Protocol (TCP), User Datagram Protocol (UDP), Datagram Congestion Control Protocol (DCCP), Stream Control Transmission. Protocol (SCTP), HyperText Markup Language (HTML), and/or the like.

As will be appreciated, one or more of the data object computing entity's components may be located remotely from components of other data object computing entities 105, such as in a distributed system. Furthermore, one or more of the components may be aggregated and additional components performing functions described herein may be included in the data object computing entity 105. Thus, the data object computing entity 105 can be adapted to accommodate a variety of needs and circumstances.

b. Exemplary Client Computing Entity

FIG. 3 provides an illustrative schematic representative of one of the client computing entities 101A to 101N that can be used in conjunction with embodiments of the present disclosure. As will be recognized, the client computing entity may be operated by an agent and include components and features similar to those described in conjunction with the data object computing entity 105. Further, as shown in FIG. 3, the client computing entity may include additional components and features. For example, the client computing entity 101A can include an antenna 312, a transmitter 304 (e.g., radio), a receiver 306 (e.g., radio), and a processing element 30 that provides signals to and receives signals from the transmitter 304 and receiver 306, respectively. The signals provided to and received from the transmitter 304 and the receiver 306, respectively, may include signaling information/data in accordance with an air interface standard of applicable wireless systems to communicate with various entities, such as a data object computing entity 105, another client computing entity 101A, and/or the like. In this regard, the client computing entity 101A may be capable of operating with one or more air interface standards, communication protocols, modulation types, and access types. More particularly, the client computing entity 101A may comprise a network interface 320, and may operate in accordance with any of a number of wireless communication standards and protocols. In a particular embodiment, the client computing entity 101A may operate in accordance with multiple wireless communication standards and protocols, such as GPRS, CDMA1900, 1×RTT, WCDMA, TD-SCDMA, LTE, E-UTRAN, EVDO, HSPA, HSDPA, Wi-Fi, WiMAX, UWB, IR protocols, Bluetooth protocols, USB protocols, and/or any other wireless protocol.

Via these communication standards and protocols, the client computing entity 101A can communicate with various other entities using Unstructured Supplementary Service data (USSD), Short Message Service (SMS), Multimedia Messaging Service (MMS), Dual-Tone Multi-Frequency (DTMF) Signaling, Subscriber Identity Module Dialer (SIM dialer), and/or the like. The client computing entity 101A can also download changes, add-ons, and updates, for instance, to its firmware, software (e.g., including executable instructions, applications, program modules), and operating system.

According to one embodiment, the client computing entity 101A may include location determining aspects, devices, modules, functionalities, and/or similar words used herein interchangeably. For example, the client computing entity 101A may include outdoor positioning aspects, such as a location module adapted to acquire, for example, latitude, longitude, altitude, geocode, course, direction, heading, speed, UTC, date, and/or various other information/data. In one embodiment, the location module can acquire data, sometimes known as ephemeris data, by identifying the number of satellites in view and the relative positions of those satellites. The satellites may be a variety of different satellites, including Low Earth Orbit (LEO) satellite systems, Department of Defense (DOD) satellite systems, the European Union Galileo positioning systems, the Chinese Compass navigation systems, Indian Regional Navigational satellite systems, and/or the like. Alternatively, the location information/data/data may be determined by triangulating the position in connection with a variety of other systems, including cellular towers, Wi-Fi access points, and/or the like. Similarly, the client computing entity 101A may include indoor positioning aspects, such as a location module adapted to acquire, for example, latitude, longitude, altitude, geocode, course, direction, heading, speed, time, date, and/or various other information/data. Some of the indoor aspects may use various position or location technologies including Radio-Frequency Identification (RFID) tags, indoor beacons or transmitters, Wi-Fi access points, cellular towers, nearby computing devices (e.g., smartphones, laptops) and/or the like. For instance, such technologies may include iBeacons, Gimbal proximity beacons, Bluetooth Low Energy (BLE) transmitters, Near Field Communication (NFC) transmitters, and/or the like. These indoor positioning aspects can be used in a variety of settings to determine the location of someone or something to within inches or centimeters.

The client computing entity 101A may also comprise a user interface comprising one or more user input/output interfaces (e.g., a display 316 and/or speaker/speaker driver coupled to a processing element 308 and a touch screen, keyboard, mouse, and/or microphone coupled to a processing element 308). For example, the user output interface may be configured to provide an application, browser, user interface, dashboard, webpage, and/or similar words used herein interchangeably executing on and/or accessible via the client computing entity 101A to cause display or audible presentation of information/data and for user interaction therewith via one or more user input interfaces. The user output interface may be updated dynamically from communication with the data object computing entity 105. The user input interface can comprise any of a number of devices allowing the client computing entity 101A to receive data, such as a keypad 318 (hard or soft), a touch display, voice/speech or motion interfaces, scanners, readers, or other input device. In embodiments including a keypad 318, the keypad 318 can include (or cause display of) the conventional numeric (0-9) and related keys (#, *), and other keys used for operating the client computing entity 101A and may include a full set of alphabetic keys or set of keys that may be activated to provide a full set of alphanumeric keys. In addition to providing input, the user input interface can be used, for example, to activate or deactivate certain functions, such as screen savers and/or sleep modes. Through such inputs the client computing entity 101A can collect information/data, user interaction/input, and/or the like.

The client computing entity 101A can also include volatile storage or memory 322 and/or non-volatile storage or memory 324, which can be embedded and/or may be removable. For example, the non-volatile memory may be ROM, PROM, EPROM, EEPROM, flash memory, MMCs, SD memory cards, Memory Sticks, CBRAM, PRAM, FeRAM, RRAM, SONOS, racetrack memory, and/or the like. The volatile memory may be RAM, DRAM, SRAM, FPM DRAM, EDO DRAM, SDRAM, DDR SDRAM, DDR2 SDRAM, DDR3 SDRAM, RDRAM, RIMM, DIMM, SIMM, VRAM, cache memory, register memory, and/or the like. The volatile and non-volatile storage or memory can store databases, database instances, database management system entities, data, applications, programs, program modules, scripts, source code, object code, byte code, compiled code, interpreted code, machine code, executable instructions, and/or the like to implement the functions of the client computing entities 101A-101N.

c. Exemplary Networks

In one embodiment, the networks 103 may include, but are not limited to, any one or a combination of different types of suitable communications networks such as, for example, cable networks, public networks (e.g., the Internet), private networks (e.g., frame-relay networks), wireless networks, cellular networks, telephone networks (e.g., a public switched telephone network), or any other suitable private and/or public networks. Further, the networks 103 may have any suitable communication range associated therewith and may include, for example, global networks (e.g., the Internet), MANs, WANs, LANs, or PANs. In addition, the networks 103 may include medium over which network traffic may be carried including, but not limited to, coaxial cable, twisted-pair wire, optical fiber, a hybrid fiber coaxial (HFC) medium, microwave terrestrial transceivers, radio frequency communication mediums, satellite communication mediums, or any combination thereof, as well as a variety of network devices and computing platforms/systems provided by network providers or other entities.

Further, the networks 103 may utilize a variety of networking protocols including, but not limited to, TCP/IP based networking protocols. In some embodiments, the protocol is a custom protocol of JavaScript Object Notation (JSON) objects sent via a WebSocket channel. In some embodiments, the protocol is JSON over RPC, JSON over REST/HTTP, and/or the like.

III. Exemplary Operation

Reference will now be made to FIGS. 4, 5, 6A, 6B, 7, 8, 9, 10, 11, 12, and 13, which provide flowcharts and diagrams illustrating example steps, processes, procedures, and/or operations associated with a natural language processing and machine learning platform/system and/or a data object computing entity in accordance with various embodiments of the present disclosure.

While example embodiments of the present disclosure may be described in the context of healthcare, a person of ordinary skill in the relevant technology will recognize that embodiments of the present disclosure are not limited to this context only.

a. Overview and Technical Advantages

As described above, natural language processing and machine learning systems and methods have great potential for providing various technical advancement and technical benefits not only in the field of computer science, but also in other associated technical fields and applications.

One of the key goals of many companies and corporations is to improve the efficiency of business processes, including those involving customer service. Many business processes require determining a result based at least in part on an understanding of multiple contracts, including how the contracts interact with each other as well as with external events.

In the context of healthcare, a "patient" may refer to an individual who received healthcare service and/or is covered under a health insurance plan (for example, but not limited to, an insurance policy holder through independent subscription to a health insurance policy or through coverage extension by another policyholder). A "health insurance provider" may refer to an entity that offers one or more health insurance plans to a patient. A "healthcare provider" may refer to an individual (for example, a physician) or an entity that provides or renders healthcare services to a patient. In some examples, a health insurance provider may require certain medical procedures, medications and/or medical tests to be evaluated (for example, to assess whether there is a medical necessity for such procedures/medications/tests) before a healthcare provider can prescribe or provide such medical procedures, medications and/or medical tests to a patient under the health insurance plan provided by the health insurance provider. As such, the healthcare provider may submit a preauthorization request to the health insurance provider to request evaluation and/or authorization of such procedures/medications/tests. The responses to preauthorization requests may depend on analyzing a couple of documents, for example but not limited to: (1) a contract between the healthcare provider and the health insurance provider that specifies, among other things, whether the healthcare provider is qualified to prescribe or provide the procedures/medications/tests and under what circumstances can the healthcare provider do so; (2) a contract between the patient and the health insurance provider that specifies, among other things, whether the patient is qualified to receive the procedures/medications/tests and, if so, under what circumstances; and/or (3) medical records that may indicate whether the patient exhibits the circumstances under which the healthcare provider would be authorized to perform the procedure.

Manually cross-referencing two contracts against a patient's medical record to determine whether the preauthorization should be granted can be a slow and costly process, and can be error-prone. Implementing natural language processing and machine learning systems and methods that would fully or partially automate such contract-based determinations can decrease the time and cost of making the determination, and may further increase the accuracy rate of such determinations. However, many natural language processing and machine learning systems and methods are plagued by many technical limitations and deficiencies.

For example, data that comprises unformatted natural language (such as that found in contracts) does not yield very accurate predictions in machine learning environments at least due to their unformatted structure. In particular, machine learning models in many machine learning environments require input data to be formatted in such as a way that can be easily ingested by the machine learning models, and data that comprises unformatted natural language fails to meet this requirement and causes decline in the accuracy of outputs (such as predictions) generated by machine learning models. Accuracy of output of machine learning models is imperative in the many contexts, including, but not limited to, healthcare context.

Various embodiments of the present disclosure overcome such technical limitations and deficiencies. For example, various embodiments of the present disclosure define a graph-based format for data that would improve the accuracy of predictions and/or decision determinations based at least in part on natural language documents (such as, but not limited to, contracts, medical records, and/or others) by machine learning models.

A graph-based format may be one that expresses information in terms of nodes and edges. Such information is often visualized as a network of nodes represented by points, which are connected by edges represented by lines. In a computing context, a graph-based format groups data in sets of three entries in which two of the entries represent names of nodes and the third represents a type of edge. Graph-based formats are useful for representing and analyzing relationships (represented by edges) between a set of concepts (represented by nodes). So, for example, a node representing "infection" and a node representing "antibiotics" might be connected by an edge of the type "treats." Graph-based data may be more complex than the simple triplet model. For example, nodes may be categorized by type. In the example above, "infection" may be categorized as node type "disease" and "antibiotic" may be categorized as node type "treatment." Formatting of data sets can become more complex so long as it is interpreted correctly by the system and includes two nodes connected by an edge. By encoding natural language data (such as, but not limited to, contracts, medical records, and/or the like) into a graph-based format and providing the graph-based data into a machine learning model, the accuracy of outcomes from the machine learning model can be improved.

While graph-based data format provides various technical benefits, encoding natural language data into a graph-based data format can be time-consuming and error-prone. For example, manually encoding natural language data (such as, but not limited to, contracts, medical records, and/or the like) is a slow process and can be labor intensive.

Various embodiments of the present disclosure overcome such technical limitations and deficiencies. For example, various embodiments of the present disclosure provide variations on machine learning techniques (such as, but not limited to, BERT (Bidirectional Encoder Representations from Transformers)) to automate the conversion of natural language data into a graph-based format. A BERT-like model could, for example, identify key concepts in natural language text (corresponding to nodes) and make informed predictions as to relationships between those concepts (edge types). In some examples, machine learning models could be validated against limited graph-based data sets curated by humans before being applied to much larger sets of natural language data.

For example, in a healthcare context, these machine learning techniques may be applied to tasks such as making determinations about medical claim preauthorization as in the above example. In a computing environment, a method for determining preauthorization may start when a data object computing entity receives a request for a determination. In some examples, the request would include a procedure name or procedure code to be authorized, an identifier of a patient to receive the procedure, and an identifier of a provider to perform the procedure. The data object computing entity would then access stored medical records related to the patient and stored contracts for which either the patient or the provider is a party (including, but not limited to, insurance policies and provider agreements). In some examples, irrelevant documents, such as contracts that have expired, could be removed from the data set based at least in part on, for example, algorithmic comparison of expiration dates in the contracts with a current date by the data object computing entity. The contracts and medical records may each be encoded in graph-based format using BERT-like models as described above.

In some embodiments, the relevant contracts and medical records will share some common nodes such as, for example, nodes representing procedures and prerequisite conditions (e.g. diagnosis codes). For example, a node in a contractual graph representing "knee replacement" may be connected to a node labeled "permanent knee damage" with a unidirectional edge of type "prerequisite." If a graph of medical records connected a node representing the patient with the node for "permanent knee damage" with an edge of type "exhibits," the contractual graph would be connected to the medical record graph in a way that could facilitate an automated decision.

Various embodiments of the present disclosure provide multiple processing strategies associated with machine learning models that can be used to determine the outcome recommendation. For example, embodiments of the present disclosure may implement supervised strategies on machine learning models by using training data that comprises graph-based data for contracts and medical records, together with human-determined preauthorization outcomes for the same or similar procedures as that of the preauthorization request. After training the supervised model on this training data, the model would be applied to the information associated with a new preauthorization request to make the outcome recommendation.

Additionally, or alternatively, unsupervised models can be used to determine an outcome recommendation. For example, embodiments of the present disclosure may apply unsupervised models to tasks such as determining the probability that an edge exists between two nodes. The unsupervised models may make such predictions using the graph networks for the patient, provider, and procedure in question without the use of training data. As an example, if an unsupervised model predicted high probabilities of "authorize" edges connecting the procedure node to each of the nodes for the patient and provider, the model may generate an output recommending, preauthorization (e.g. recommending approving the procedure).

In accordance with various embodiments of the present disclosure, outputs from data prediction machine learning models may take the form of probabilities rather than a discrete recommendation (e.g. approve or deny). In some embodiments, outputs whose confidence level exceeds a threshold may be accepted without further human review. In some embodiments, thresholds may be different for some outcomes (e.g. approval) than for others (e.g. denial). In some embodiments, confidence levels below the relevant thresholds may be tagged for further review by humans. As human determinations generate more training data (for supervised models) and confidence in the methods increase with modification and testing, the outputs may become discrete (e.g. approve or deny).

While the description above provides an example in the context of healthcare, it is noted that the scope of the present disclosure is not limited to the healthcare context only. As an example from the insurance industry, graph-based encoding of natural language could be applied to auto insurance policies and police accident reports to make determinations as to whether collision repair should be covered by the policy. Outputs could be based at least in part on the presence or absence of multiple edge types. For example, outputs could include indicators to escalate a case to a higher authority level, transfer it to a different department, or recommend an alternate procedure for treatment. The speed with which automated determinations are made could substantially improve the customer service experience. Additionally, or alternatively, while the example above illustrate making individual decisions based at least in part on contracts, example embodiments of the present disclosure include decisions that could flow in the opposite direction (for example, make automated recommendations as to which providers should be in a coverage network, how to price patient and provider contracts, and/or the like).

As such, various embodiments of the present disclosure overcome technical challenges, deficiencies and problems associated with natural language processing and machine learning systems and methods, and provide various technical benefits, details of which are described herein.

b. Definitions

In the present disclosure, the term "data object" may refer to a data structure that comprises, represents, indicates, and/or is associated with one or more attributes, functionalities and/or characteristics associated with data and/or information in an example natural language processing and machine learning platform/system. In some embodiments, a data object may be in the form of one or more regions in one or more data storage devices (such as, but not limited to, a computer-readable storage medium) that comprise one or more values (such as, but not limited to, one or more identifiers, one or more metadata, and/or the like). In some embodiments, an example data object may comprise or be associated with one or more identifiers, one or more metadata, and/or one or more other data objects. In accordance with various embodiments of the present disclose, example data objects may be categorized based at least in part on their corresponding types and/structures, including, but not limited to, a natural language data object, a graph-based data object, and/or the like.

In the present disclosure, the term "natural language data object" may refer to a data object that indicates, comprises, represents, and/or is associated with natural language data (e.g., text data). The natural language data may indicate, comprise, and/or represent data and/or information that is in the format of natural language that has been developed naturally in use by humans (as contrasted to an artificial language or a computer code that is programmatically generated). Examples of natural language data objects include, but not limited to, medical record data objects, textual contract data objects, and/or the like.

In the present disclosure, the term "medical record data object" may refer to a data object that indicates, comprises, represents, and/or is associated with one or more medical records associated with one or more patients. In some embodiments, an example medical record data object may be in the form of and/or comprise one or more electronic medical records ("EMRs"), which indicates, comprises, represents, and/or is associated with data and information associated with one or more patients, such as, but not limited to, current health statuses or conditions of the one or more patients (for example, any current symptoms that the one or more patients may exhibit or experience, any current medications that the one or more patients may be taking), health histories of the one or more patients (for example, any symptoms that the one or more patients may have exhibited or experience in the past, any medications that the one or more patients may have taken in the past, any procedures that may have been conducted on the one or more patients, and/or the like), office visits of the one or more patients (for example, data and/or information associated with one or more visits to a doctor's office, a clinic, a pharmacy, a hospital, and/or the like to seek medical help, medical treatment, medical assistance, pharmacy prescriptions, and/or the like), and/or the like.

In the present disclosure, the term "textual contract data object" may refer to a data object that indicates, comprises, represents, and/or is associated with an agreement and/or a contract between and/or among two or more entities. Such an agreement and/or contract may define and govern the rights and duties between and/or among two or more entities (for example, exchange of goods, services, and/or promises for goods and/or services). For example, an example textual contract data object may indicate, comprise, represent, and/or is associated with a legal binding agreement between a health insurance provider and a patient, which may define duties of the patient to pay a health insurance premium and duties of the health insurance provider to provide reimbursements of certain healthcare related cost to the patient. As another example, an example textual contract data object may indicate, comprise, represent, and/or is associated with a legal binding agreement between a healthcare provider and a patient, which may define duties of the patient to pay a certain amount of cost associated with one or more healthcare services (for example, a procedure) to be rendered by the healthcare provider and duties of the healthcare provider to render such healthcare services. As another example, an example textual contract data object may indicate, comprise, represent, and/or is associated with a legal binding agreement between a healthcare provider and a health insurance provider, which may define duties of the healthcare provider to perform one or more actions with respect to one or more healthcare services that the healthcare provider offers (for example, but not limited to, submitting preauthorization requests prior to conducting certain procedures on patients) and duties of the health insurance provider to reimbursement the healthcare provider should such healthcare services be rendered on patients.

In the present disclosure, the term "graph-based data object" may refer to a data object that may be represented, processed, transmitted, and/or stored in a graph-based form/structure/format (e.g., using a set of nodes and a set of edges). For example, a graph data object may describe an ordering or arrangement of data/information as nodes and edges. In some embodiments, an example graph-based data object may be generated based at least in part on one or more natural language data objects, such as, but not limited to, medical record data objects and/or textual contract data objects, details of which are described herein.

In the present disclosure, the terms "node" or "vertex" may refer to an element of a graph-based data object that indicates, comprises, represents, and/or is associated with an entity related to the graph-based data object and/or an entity associated with the natural language data object(s) (such as, but not limited to, medical record data object(s) and/or textual contract data object(s)) based at least in part on which the graph-based data object was generated. For example, a node of a graph-based data object can be graphically depicted as a point in the graph-based data object.

In the present disclosure, each node in a graph-based data object may be associated with a "node type," which may refer to a category, a kind, a classification and/or a type of the node. In the present disclosure, node types of nodes in graph-based data objects can be categorized and/or classified based at least in part on the types of entities that are associated with the nodes.

In the present disclosure, the term "patient entity node" may refer to a category, a kind, a classification and/or a type of node in a graph-based data object that indicates, comprises, represents, and/or is associated with a patient entity related to the graph-based data object and/or associated with the natural language data object(s) (such as, but not limited to, medical record data object(s) and/or textual contract data object(s)) based at least in part on which the graph-based data object was generated.

In the present disclosure, the term "symptom node" may refer to a category, a kind, a classification and/or a type of node that indicates, comprises, represents, and/or is associated with one or more health-related symptoms of a patient entity associated with the graph-based data object and/or associated with the natural language data object(s) (such as, but not limited to, medical record data object(s) and/or textual contract data object(s)) based at least in part on which the graph-based data object was generated.

In the present disclosure, the term "health insurance provider entity node" may refer to a category, a kind, a classification and/or a type of node that indicates, comprises, represents, and/or is associated with a health insurance provider related to the graph-based data object and/or associated with the natural language data object(s) (such as, but not limited to, medical record data object(s) and/or textual contract data object(s)) based at least in part on which the graph-based data object was generated.

In the present disclosure, the term "healthcare provider entity node" may refer to a category, a kind, a classification and/or a type of node that indicates, comprises, represents, and/or is associated with a healthcare provider related to the graph-based data object and/or associated with the natural language data object(s) (such as, but not limited to, medical record data object(s) and/or textual contract data object(s)) based at least in part on which the graph-based data object was generated.

In the present disclosure, the term "procedure node" may refer to a category, a kind, a classification and/or a type of node that indicates, comprises, represents, and/or is associated with one or more medical procedures that are offered by, conducted by, rendered by, and/or otherwise related to a healthcare provide that is associated with the graph-based data object and/or associated with the natural language data object(s) (such as, but not limited to, medical record data object(s) and/or textual contract data object(s)) based at least in part on which the graph-based data object was generated.

In the present disclosure, the term "edge" may refer to an element of a graph-based data object that indicates, comprises, represents, and/or is associated with a relationship between and/or among entities associated with the graph-based data object and/or entities associated with the natural language data object(s) (such as, but not limited to, medical record data object(s) and/or textual contract data object(s)) based at least in part on which the graph-based data object was generated. For example, an edge of a graph-based data object can be graphically depicted as a line or arc connecting two or more nodes of the graph-based data object.

In the present disclosure, each edge in a graph-based data object may be associated with an "edge type," which may refer to a category, a kind, a classification and/or a type of the edge. In the present disclosure, edge types of edges in graph-based data objects can be categorized and/or classified based at least in part on the types of relationships between the entities that are associated with the nodes.

In the present disclosure, the term "machine learning model" may refer to a software computer program (and, in some embodiments, associated hardware) that is trained to process, analyze, generate, integrate, summarize, translate, and/or predict one or more output data sets based at least in part on one or more input data sets. For example, an example machine learning model may be trained to recognize patterns in the one or more input data sets, identify trends from the one or more input data sets, generate one or more predictions based at least in part on the one or more input data sets, and/or the like. Examples of machine learning models may include, but are not limited to, artificial neural networks, linear regression models, logistic regression models, decision tree models, naive bayes models, and/or the like.

In some embodiments, an example machine learning model may comprise one or more sub-models. In some embodiments, each sub-model is a part of the example machine learning model, and may exchange data and/or information to/from/with another sub-model and/or another machine learning model to generate the one or more output data sets based at least in part on the one or more input data sets. In some embodiments, each sub-model of an example machine learning model may be associated with a particular function of the example machine learning model.

In some embodiments, an example machine learning model and/or an example sub-model of the example machine learning model may generate one or more "classifications." In the present disclosure, the term "classification" may refer to one or more output data sets generated by a machine learning model and/or a sub-model that indicates, comprises, represents, and/or is associated with a predicted category, a predicted kind, a predicted classification, a predicted type, predicted name, a predicted identifier, and/or the like associated with one or more input data sets provided to the machine learning model and/or the sub-model.

In the present disclosure, the term "entity extraction machine learning model" may refer to a category, a kind, a classification and/or a type of machine learning model that encodes natural language data objects (such as, but not limited to, medical record data objects and/or textual contract data objects), and extracts entity data/information and/or entity relationship data/information from natural language data objects (such as, but not limited to, medical record data objects and/or textual contract data objects). In some embodiments, the entity extraction machine learning model is part of a machine learning framework that encodes natural language data objects (such as, but not limited to, medical record data objects and/or textual contract data objects), extracts entity data/information from natural language data objects (such as, but not limited to, medical record data objects and/or textual contract data objects); extracts entity relationship data/information from natural language data objects (such as, but not limited to, medical record data objects and/or textual contract data objects), and/or generates one or more graph-based data objects based at least in part on the natural language data objects (such as, but not limited to, medical record data objects and/or textual contract data objects). In some embodiments, inputs to an entity extraction model include an array or a linked list describing a string, while outputs of the entity extraction may include an array describing one or more graph-based data objects and/or one or more entities.

As described above, an example machine learning model may comprise a plurality of sub-models. In some examples, an example entity extraction machine learning model in accordance with various embodiments of the present disclosure may include, but not limited to, an encoder sub-model, an entity classification sub-model, and/or an entity relationship classification sub-model.

In the present disclosure, the term "encoder sub-model" may refer to a category, a kind, a classification and/or a type of sub-model of an entity extraction machine learning model that transfers/converts data and/or information from natural language data objects (such as, but not limited to, medical record data objects and/or textual contract data objects) into text embeddings. In the present disclosure, the term "text embedding" may refer to a representation for one or more words, one or more phrases, and/or one or more texts of a natural language data object (such as, but not limited to, medical record data objects and/or textual contract data objects) in a vector space. In some embodiments, an example text embedding may be in the form of a real-valued vector that encodes the meaning of one or more words, one or more phrases, and/or one or more texts of a natural language data object, such that text embeddings associated with word(s), phrase(s), and/or text(s) to be similar in meaning are closer with one another in the vector space. In some embodiments, inputs to an encoder sub-model include an array or a linked list describing a string, while outputs of the encoder sub-model include an encoding output vector.

In various embodiments of the present disclosure, an example encoder sub-model may be in various different forms and/or be trained in different ways. Examples of encoder sub-models may include, but not limited to, one or more Bi-directional Encoder Representations from Transformer (BERT) trained models, one or more artificial neural networks, one or more binary encoder models, one or more Term Frequency (TF) encoder models, one or more Term Frequency-Inverse Document Frequency (TF-IDF) encoder models, one or more Word2Vec encoder models, and/or the like.

For example, BERT provides an example method of training an encoder sub-model. In some embodiments, BERT creates training data sets by randomly removing data points from more complete data sets, and trains the encoder sub-model to predict the complete data based at least in part on incomplete data. In some embodiments, the training of the encoder sub-model is bi-directional in that it can use data/information both before and after a missing element to predict the missing element. In the present disclosure, an encoder sub-model that has been trained using BERT is also referred to as a BERT trained encoder sub-model.

In the present disclosure, the encoder sub-model is associated with a multi-headed attention mechanism. Continuing from the above example, an example BERT trained encoder sub-model may comprise one or more "layers," where each layer of the example BERT trained encoder sub-model is configured to perform one or more natural language processing tasks. For example, the example BERT trained encoder sub-model may comprise a multi-head attention layer, a feed forward layer, and one or more add & norm layers. In some embodiments, the multi-head attention layer may utilize a multi-head attention mechanism. In particular, the multi-head attention mechanism may cause data and/or information from natural language data object(s) (such as, but not limited to, medical record data object(s) and/or textual contract data object(s)) to run through the multi-head attention layer multiple times in parallel to transform and/or convert data and/or information from natural language data object(s) into one or more attention vectors. In some embodiments, the feed forward layer may transform the attention vectors into another form that is suitable for the next layer/transformer. In some embodiments, an add & norm layer may follow the multi-head attention layer, and an add & norm layer may follow the feed forward layer. In some embodiments, each of the add & norm layers may normalize the output from the prior layer to generate one or more text embeddings based at least in part on the natural language data object(s) (such as, but not limited to, medical record data object(s) and/or textual contract data object(s)).

In the present disclosure, the term "entity classification sub-model" may refer to a category, a kind, a classification and/or a type of sub-model of an entity extraction machine learning model that determines entity classifications based at least in part on text embeddings. In the present disclosure, the term "entity classification" may refer to a category, a kind, a classification and/or a type of classification that is generated by an entity classification sub-model and indicates, comprises, represents, and/or is associated with one or more entities related to natural language data object(s) (such as, but not limited to, medical record data object(s) and/or textual contract data object(s)). In the present disclosure, examples of entities include, but are not limited to, a healthcare provider, a health insurance provider, a patient, a medical procedure, a symptom of the patient, and/or the like.

In various embodiments of the present disclosure, an example entity classification sub-model may be in various different forms and/or be trained in different ways. Examples of entity classification sub-model may include, but not limited to, one or more artificial neural networks, deep learning networks, and/or the like. Additionally, or alternatively, the entity classification sub-model may be trained based at least in part on BERT, similar to those described above.

For example, to generate the entity classifications, the entity classification sub-model may comprise at least three layers: an input layer, one or more hidden layer(s), and an output layer. In this example, the input layer receives text embeddings, the one or more hidden layer(s) extracts entity classifications from the text embeddings, and the output layer provides extracted entity classifications as outputs of the entity classification sub-model.

While the description above provides an example structure of an entity classification sub-model, it is noted that the scope of the present disclosure is not limited to the description above. In some examples, an example entity classification sub-model may comprise one or more additional and/or alternative elements.

In the present disclosure, the term "entity identifier" may refer to an identifier that uniquely identifies an entity associated with the natural language data object(s) (such as, but not limited to, medical record data object(s) and/or textual contract data object(s)). In some embodiments, the entity identifier may be in the form of text string(s), numerical character(s), alphabetical character(s), alphanumeric code(s), American Standard Code for Information Interchange (ASCII) character(s), and/or the like.

In the present disclosure, the term "healthcare provider entity identifier" may refer to a category, a kind, a classification and/or a type of entity identifier that uniquely identifies a healthcare provider associated with the natural language data object(s) (such as, but not limited to, medical record data object(s) and/or textual contract data object(s)).

In some embodiments, the healthcare provider entity identifier may be in the form of text string(s), numerical character(s), alphabetical character(s), alphanumeric code(s), ASCII character(s), and/or the like.

In the present disclosure, the term "health insurance provider entity identifier" may refer to a category, a kind, a classification and/or a type of entity identifier that uniquely identifies a health insurance provider associated with the natural language data object(s) (such as, but not limited to, medical record data object(s) and/or textual contract data object(s)). In some embodiments, the health insurance provider entity identifier may be in the form of text string(s), numerical character(s), alphabetical character(s), alphanumeric code(s), ASCII character(s), and/or the like.

In the present disclosure, the term "patient entity identifier" may refer to a category, a kind, a classification and/or a type of entity identifier that uniquely identifies a patient associated with the natural language data object(s) (such as, but not limited to, medical record data object(s) and/or textual contract data object(s)). In some embodiments, the patient entity identifier may be in the form of text string(s), numerical character(s), alphabetical character(s), alphanumeric code(s), ASCII character(s), and/or the like.

In the present disclosure, the term "procedure identifier" may refer to a category, a kind, a classification and/or a type of entity identifier that uniquely identifies a medical procedure associated with natural language data object(s) (such as, but not limited to, medical record data object(s) and/or textual contract data object(s)). In some embodiments, the procedure identifier may be in the form of text string(s), numerical character(s), alphabetical character(s), alphanumeric code(s), ASCII character(s), and/or the like.

While the description above provides some examples of entity identifiers, it is noted that the scope of the present disclosure is not limited to the description above. Additional examples of entity identifiers may include, but are not limited to, symptom identifier that uniquely identifies a health symptom, medication identifier that uniquely identifies a medication, and/or the like.

In the present disclosure, the term "entity pair" may refer to two entities as represented by two entity identifiers.

In the present disclosure, the term "entity relationship classification sub-model" may refer to a category, a kind, a classification and/or a type of sub-model of an entity extraction machine learning model that determines an entity relationship classification of an entity pair based at least in part on, for example but not limited to, at least text embeddings generated by an encoder sub-model and/or at least entity classifications generated by an entity classification sub-model. In the present disclosure, the term "entity relationship classification" may refer to a category, a kind, a classification and/or a type of classification that is generated by an entity relationship classification sub-model and indicates, comprises, represents, and/or is associated with one or more relationships between and/or among two or more entities associated with natural language data object(s) (such as, but not limited to, medical record data object(s) and/or textual contract data object(s)). In some embodiments, inputs to an entity relationship classification sub-model include a pair of vectors, each corresponding to the encoding of an entity, while outputs of an entity relationship classification sub-model include a vector describing entity relationship classification for the pair.

In various embodiments of the present disclosure, an example entity relationship classification sub-model may be in various different forms and/or be trained in different ways. Examples of entity relationship classification sub-model may include, but not limited to, one or more artificial neural networks, deep learning networks, and/or the like. Additionally, or alternatively, the entity relationship classification sub-model may be trained based at least in part on BERT, similar to those described above.

For example, to generate the entity relationship classifications, the entity relationship classification sub-model may comprise at least three layers: an input layer, one or more hidden layer(s), and an output layer. In this example, the input layer receives text embeddings, the one or more hidden layer(s) extracts entity relationship classifications from the text embeddings, and the output layer provides extracted entity relationship classifications as outputs from the entity relationship classification sub-model.

While the description above provides an example structure of an entity relationship classification sub-model, it is noted that the scope of the present disclosure is not limited to the description above. In some examples, an example entity relationship classification sub-model may comprise one or more additional and/or alternative elements.

In the present disclosure, the term "entity relationship identifier" may refer to an identifier that uniquely identifies an entity relationship from other entity relations. In some embodiments, the entity relationship identifier may be in the form of text string(s), numerical character(s), alphabetical character(s), alphanumeric code(s), ASCII character(s), and/or the like.

In accordance with various embodiments of the present disclosure, an example computing entity (such as the client computing entity and the data object computing entity) may receive one or more electronic requests from another computing entity, may generate one or more electronic requests, and may transmit one or more electronic requests to another computing entity. Examples of electronic requests in accordance with various embodiments of the present disclosure may include, but are not limited to, data prediction requests (including preauthorization requests), data prediction review requests, and/or the like.

In the present disclosure, the term "data prediction request" may refer to an electronic request (for example, generated by and/or transmitted from a client computing device) to generate one or more data predictions based at least in part on one or more natural language data objects and/or on one or more graph-based data objects that are generated based at least in part on the one or more natural language data objects.

For example, an example data prediction request may be associated with a preauthorization request. In the present disclosure, the term "preauthorization request" may refer to a category, a kind, a classification and/or a type of electronic request that comprises, indicates, represents, and/or is associated with a request to a health insurance provider to approve one or more medical procedures, one or more medical tests, one or more medications, and/or the like to be provided to or be rendered on a patient by a healthcare provider. In such an example, the data prediction request associated with the preauthorization request may indicate/comprise an electronic request to predict or estimate whether the preauthorization request will be or should be approved by the health insurance provider, and/or the likelihood that the health insurance provider will or should approve the preauthorization request.

In the present disclosure, the term "data prediction review request" may refer to a type of electronic request that comprises, indicates, represents, and/or is associated with an electronic request to a user (for example, transmitted to a client computing entity) to manually review at least one prediction data object (as defined herein) generated in accordance with various embodiments of the present disclosure.

In the present disclosure, the term "prediction-based action" may refer to a category, a kind, a classification and/or a type of computer operation to generate prediction data based at least in part on a graph-based data object that is generated in accordance with various embodiments of the present disclosure.

In the present disclosure, the term "data prediction machine learning model" may refer to a category, a kind, a classification and/or a type of machine learning model that generates prediction data (such as, but not limited to, prediction data objects) based at least in part on a graph-based data object and/or a sub-graph of the graph-based data object.

In the present disclosure, the term "prediction data object" may refer to a category, a kind, a classification and/or a type of data object that comprises, represents, indicates, and/or is associated with at least one predicted or estimated outcome (for example, an outcome of various requests described herein, including, but not limited to, preauthorization requests).

In the present disclosure, the term "prediction confidence score" may refer to a confidence level or likelihood associated with the predicted or estimated outcome that is represented by, is indicated by, and/or is associated with a prediction data object. For example, the prediction confidence score may indicate a programmatically determined possibility level that the predicted or estimated outcome represented by, indicated by, and/or associated with the prediction data object is correct or true.

In the present disclosure, the term "data prediction threshold" may refer to a threshold level or value that is associated with a prediction confidence score of a prediction data object. For example, the data prediction threshold may set or indicate a baseline confidence level of a prediction data object that can be tolerated by the natural language processing and machine learning platform/system, details of which are described herein.

In the present disclosure, the term "recommendation data object" may refer to a category, a kind, a classification and/or a type of data object that comprises data and/or information that represents, indicates, and/or is associated with one or more recommended and/or suggested operations (such as, but not limited to, operations in response to various electronic requests described herein). In some embodiments, an example recommendation data object may be generated based at least in part on at least one prediction data object, details of which are described herein.

In the present disclosure, the term "training data set" may refer to a set of data that is utilized for training various machine learning models described herein, including, but not limited to, data prediction machine learning models.

For example, an example training data set for training a data prediction machine learning model may include pairs of historical data prediction requests and historical response data objects. In particular, each of the historical data prediction requests corresponds to one of the historical response data objects.

In the present disclosure, the term "historical data prediction request" may refer to a historical electronic request (for example, generated by and/or transmitted from a client computing device) to generate one or more data predictions based at least in part oil one or more natural language data objects and one or more graph-based data objects that are generated based at least in part on the one or more natural language data objects. In the present disclosure, the term "historical response data object" may refer to a category, a kind, a classification and/or a type of historical data object that indicates, represents, and/or describes a response or an outcome to a historical data prediction request (for example, an actual response to a historical data predication request made by a reviewer through manually reviewing the request, an actual outcome of the historical data prediction request, and/or the like).

c. Exemplary Techniques For Determining Entity Identifiers And Relationship Identifiers As described above, there are technical challenges, deficiencies and problems associated with natural language processing and machine learning systems and methods, and various example embodiments of the present disclosure overcome such challenges. For example, referring now to FIG. 4, an example method 400 of generating a graph-based data object (based at least in part on a plurality of natural language data objects) and performing one or more prediction-based actions based at least in part on the graph-based data object in accordance with embodiments of the present disclosure is illustrated. As such, the example method 400 overcomes various technical challenges.

For example, the example method 400 determines a plurality of entity identifiers for the plurality of natural language data objects based at least in part on implementing an encoder sub-model and an entity classification sub-model of an entity extraction machine learning model. In some embodiments, the example method 400 determines a plurality of entity relationship identifiers for the plurality of natural language data objects based at least in part on implementing an entity relationship classification sub-model of the entity extraction machine learning model.

Figure 4:
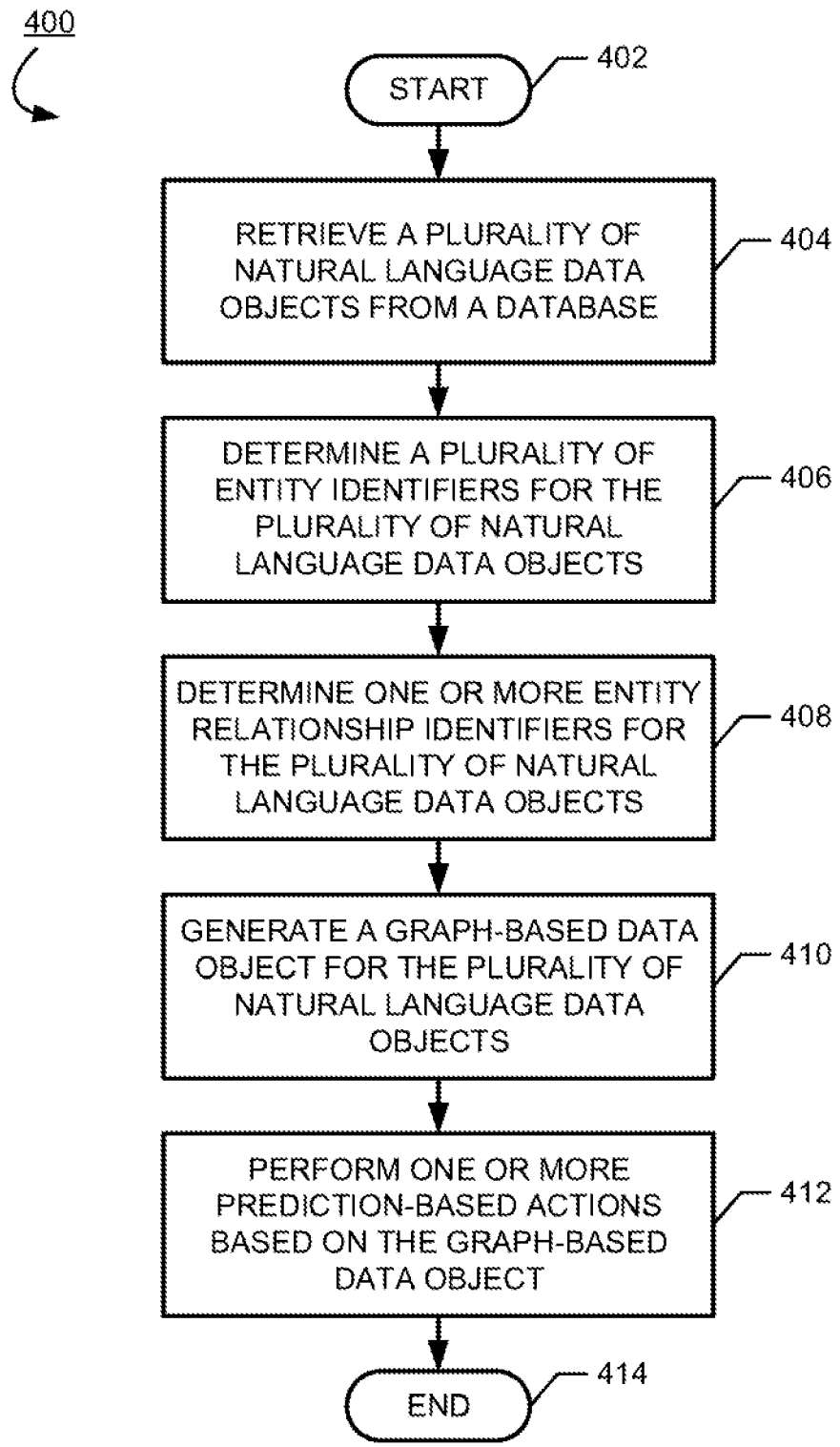

As shown in FIG. 4, the example method 400 starts at step/operation 402. Subsequent to and/or in response to step/operation 402, the example method 400 proceeds to step/operation 404. At step/operation 404, a computing entity (such as the data object computing entity 105 described above in connection with FIG. 1 and FIG. 2) may include means (such as the processing element 205 of the data object computing entity 105 described above in connection with FIG. 2) to retrieve a plurality of natural language data objects from a database.

In some embodiments, the plurality of natural language data objects may be retrieved by the processing element from a database that is internal and/or a part of a natural language processing and machine learning platform/system (for example, the natural language processing and machine learning platform/system 100 described above in connection with at least FIG. 1). In some embodiments, the plurality of natural language data objects may be retrieved by the processing element from a database that is external to a natural language processing and machine learning platform/system (for example, the natural language processing, and machine learning platform/system 100 described above in connection with at least FIG. 1).

In some embodiments, the plurality of natural language data objects may comprise medical record data objects and/or textual contract data objects. As described above, the medical record data object may indicate, comprise, represent, and/or be associated with one or more medical records associated with one or more patients. The textual contract data object may indicate, comprise, represent, and/or be associated with an agreement and/or a contract between and/or among two or more entities, such as, but not limited to, one or more patients, one or more healthcare providers, one or more health insurance providers, and/or the like.

As an example, the processing element may retrieve a medical record data object that corresponds to a medical record of a patient John, a first textual contract data object corresponds to an insurance agreement between the patient John and a health insurance provider Acme Insurance, and a second textual contract data object corresponds to an agreement between the health insurance provider Acme Insurance and a healthcare provider Beta Health.

Referring back to FIG. 4, subsequent to and/or in response to step/operation 404, the example method 400 proceeds to step/operation 406. At step/operation 406, a computing entity (such as the data object computing entity 105 described above in connection with FIG. 1 and FIG. 2) may include means (such as the processing element 205 of the data object computing entity 105 described above in connection with FIG. 2) to determine a plurality of entity identifiers for the plurality of natural language data objects.

In some embodiments, the processing element may determine the plurality of entity identifiers based at least in part on the plurality of natural language data objects retrieved at step/operation 404 and by utilizing an entity extraction machine learning model. As described above, the entity extraction machine learning model comprises an encoder sub-model and an entity classification sub-model.

In some embodiments, the encoder sub-model is configured to generate a plurality of text embeddings based at least in part on the plurality of natural language data objects. As described above, text embeddings provide representations of one or more words, one or more phrases, and/or one or more texts of a natural language data object in a vector space. In some embodiments, to generate the one or more text embeddings, the encoder sub-model may be a BERT trained encoder sub-model that comprises a multi-head attention layer and implements a multi-head attention mechanism, as described above. For example, the BERT trained encoder sub-model may map sets of word(s), phrase(s), and/or text(s) to vector(s) from natural language data objects in the vector space, where a distance between vectors are based at least in part on the similarities in meaning of such word(s), phrase(s), and/or text(s). For example, vectors for words, phrases, and/or texts that have similar meanings are placed closely with one another in the vector space, and vectors for words, phrases, and/or texts that have dissimilar meanings are placed away from one another.

While the description above provides an example of using a BERT trained encoder sub-model, it is noted that the scope of the present disclosure is not limited to the description above. In some examples, an example encoder sub-model may be in other forms and/or trained through other methods.

Continuing from the example above, the processing element may utilize the encoder sub-model of the entity extraction machine learning model to generate a plurality of text embeddings based at least in part on the medical record data object and the textual contract data object. In this example, the encoder sub-model generates text embeddings that represent words, phrases, and texts in the medical record of the patient John, the insurance agreement between the patient John and a health insurance provider Acme Health, and the agreement between the health insurance provider Acme Health and the healthcare provider Beta Health.

In some embodiments, the entity classification sub-model is configured to determine an entity classification for each text embedding. For example, the entity classification sub-model may be trained using a training data set that comprises historical text embeddings and historical entity classifications corresponding to the historical text embeddings. During the training, the entity classification sub-model may receive the historical text embeddings, may adjust one or more of its parameters so as to generate entity classifications that match or are close to the corresponding historical entity classifications. As described above, text embeddings generated by the encoder sub-model may provide representations of words, phrases, and/or texts in natural language data objects based at least in part on their corresponding meaning. As such, the entity classification sub-model may utilize the text embeddings to determine whether words, phrases, and/or texts in natural language data objects are associated with or represent an entity so as to generate an entity classification indicating or representing an entity that is described in the natural language data object.

In some embodiments, the processing element may further determine the plurality of entity identifiers based at least in part on each entity classification. For example, the processing element may determine that entity classifications generated based at least in part on the text embeddings may comprise ones that are duplicate of another (for example, entity classifications that correspond to the same entity). The processing element may identify one or more unique entity classifications from the plurality of entity classifications, and may generate an entity identifier for each of the unique entity classifications.

Continuing from the example above, the processing element may utilize the entity classification sub-model of the entity extraction machine learning model to generate an entity classification for each text embedding that is generated by the encoder sub-model, and determine an entity identifier for each entity classification. For example, the entity classification sub-model may determine a patient entity identifier for the patient John based at least in part on text embeddings associated with the medical record data object and the first textual contract data object, determine a health insurance provider entity identifier for Acme Insurance based at least in part on text embeddings associated with the first textual contract data object and the second textual contract data object, and determine a healthcare provider entity identifier for Beta Health based at least in part on text embedding associated with the medical record data object and the second textual contract data object.

Referring back to FIG. 4, subsequent to and/or in response to step/operation 406, the example method 400 proceeds to step/operation 408. At step/operation 408, a computing entity (such as the data object computing entity 105 described above in connection with FIG. 1 and FIG. 2) may include means (such as the processing element 205 of the data object computing entity 105 described above in connection with FIG. 2) to determine one or more entity relationship identifiers for the plurality of natural language data objects.

In some embodiments, the processing element may determine the one or more entity relationship identifiers for the plurality of natural language data objects based at least in part on text embeddings generated at step/operation 406 and/or the plurality of entity identifiers determined at step/operation 406 and by utilizing the entity extraction machine learning model. As described above, the entity extraction machine learning model comprises an entity relationship classification sub-model.

In some embodiments, the entity relationship classification sub-model is configured to determine an entity relationship classification for each entity pair (e.g. two entity identifiers) from the plurality of entity identifiers determined at step/operation 406 based at least in part on a subset of the plurality of text embeddings that corresponds to the entity pair.

For example, the entity relationship classification sub-model may select two entity identifiers from the plurality of entity identifiers and determine a subset of the plurality of text embeddings generated by the encoder sub-model that correspond to these two entity identifiers. The entity classification sub-model may be trained using a training data set that comprises historical text embeddings and historical entity relationship classifications corresponding to the historical text embeddings. During the training, the entity relationship classification sub-model may receive the historical text embeddings, may adjust one or more of its parameters so as to generate entity relationship classifications that match or are close to the corresponding historical entity classifications. As described above, text embeddings generated by the encoder sub-model may provide representations of words, phrases, and/or texts in natural language data objects based at least in part on their corresponding meanings. As such, the entity relationship classification sub-model may utilize the text embeddings to determine words, phrases, and/or texts in a natural language data object that describe or indicate an entity relationship so as to generate an entity relationship classification that indicates or represents an entity relationship described in the natural language data object.

In some embodiments, the processing element determines the one or more entity relationship identifiers based at least in part on each entity relationship classification. For example, the processing element may determine that entity relationship classifications that are associated with two entities and generated based at least in part on the text embeddings may comprise ones that are duplicate of another (for example, several entity relationship classifications describing the same entity relationship between the same entities). The processing element may identify one or more unique entity relationship classifications from the plurality of entity relationship classifications, and may generate an entity relationship identifier for each of the unique entity relationship classifications.

Continuing from the example above, the processing element may utilize the entity relationship classification sub-model of the entity extraction machine learning model to determine an entity relationship classification for each entity pair from the plurality of entity identifiers based at least in part on a subset of the plurality of text embeddings that are generated by the encoder sub-model. For example, the processing element may determine an entity relationship identifier between. Beta Health and John as a doctor-patient relationship based at least in part on text embeddings associated with the medical record data object, an entity relationship identifier between Acme Insurance and John as an insurer-insured relationship based at least in part on text embedding associated with the first textual contract data object, and/or the like.

Continuing from this example, the processing element may determine one or more additional entity identifiers and/or entity relationship identifiers based at least in part on the text embeddings. For example, the processing element may determine an entity identifier that describes a symptom of "knee damage," and may determine an entity relationship identifier that describes an entity relationship between this entity identifier and the entity identifier for the patient John as "exhibit" (e.g. indicating that the patient John exhibits a symptom of knee damage).

Referring back to FIG. 4, subsequent to and/or in response to step/operation 408, the example method 400 proceeds to step/operation 410. At step/operation 410, a computing entity (such as the data object computing entity 105 described above in connection with FIG. 1 and FIG. 2) may include means (such as the processing element 205 of the data object computing entity 105 described above in connection with FIG. 2) to generate a graph-based data object for the plurality of natural language data objects.

In some embodiments, the processing element may generate a graph-based data object for the plurality of natural language data objects based at least in part on the plurality of entity identifiers determined at step/operation 406 and the one or more entity relationship identifiers determined at step/operation 408.

As described above, examples of the entity identifiers may include, but not limited to, patient entity identifiers that uniquely identify patents, healthcare provider entity identifiers that uniquely identify healthcare providers, health insurance provider entity identifiers that uniquely identify health insurance providers, procedure identifiers that uniquely identifies medical procedures, symptom identifiers that uniquely identify medical procedures, and/or the like. In some embodiments, the processing element may generate a node for each of the entity identifiers. For example, the processing element may generate a patient entity node for each patient entity identifier that is determined at step/operation 406, a healthcare provider entity node for each healthcare provider entity identifier that is determined at step/operation 406, a procedure node for each procedure identifier that is determined at step/operation 406, and/or the like.

In addition, the processing element may generate one or more edges connecting the one or more nodes based at least in part on the one or more entity relationship identifiers determined at step/operation 408. For example, for each entity relationship identifier that indicates an entity relationship between two entities, the processing dement may generate an edge that connects the nodes that represent these two entities.

Continuing from the example above, the processing element may generate a node that represents John, a node that represents Acme insurance, and a node that represents Beta Health. Based at least in part on the corresponding entity relationships described above, the processing element may generate an edge connecting the node that represents John and the node that represents Acme insurance, and generate an edge connecting the node that represents John and the node that represents Beta Health. As shown in this example, an example graph-based data object in accordance with embodiments of the present disclosure may indicate connections between different natural language data objects based at least in part on one or more shared entity identifiers that are determined from these natural language data objects. Additionally, the processing element may generate a node that represents a knee damage symptom, and may connect the node with the node that represents John.

Referring back to FIG. 4, subsequent to and/or in response to step/operation 410, the example method 400 proceeds to step/operation 412. At step/operation 412, a computing entity (such as the data object computing entity 105 described above in connection with FIG. 1 and FIG. 2) may include means (such as the processing element 205 of the data object computing entity 105 described above in connection with FIG. 2) to perform one or more prediction-based actions based at least in part on the graph-based data object.

For example, the processing element may generate prediction data (such as, but not limited to, a prediction data object in response to a data prediction request) based at least in part on the graph-based data object generated at step/operation 410, and may transmit the prediction data to a client computing entity, details of which are described herein.

Referring back to FIG. 4, subsequent to step/operation 412, the example method 400 proceeds to step/operation 414 and ends.

Figure 5:
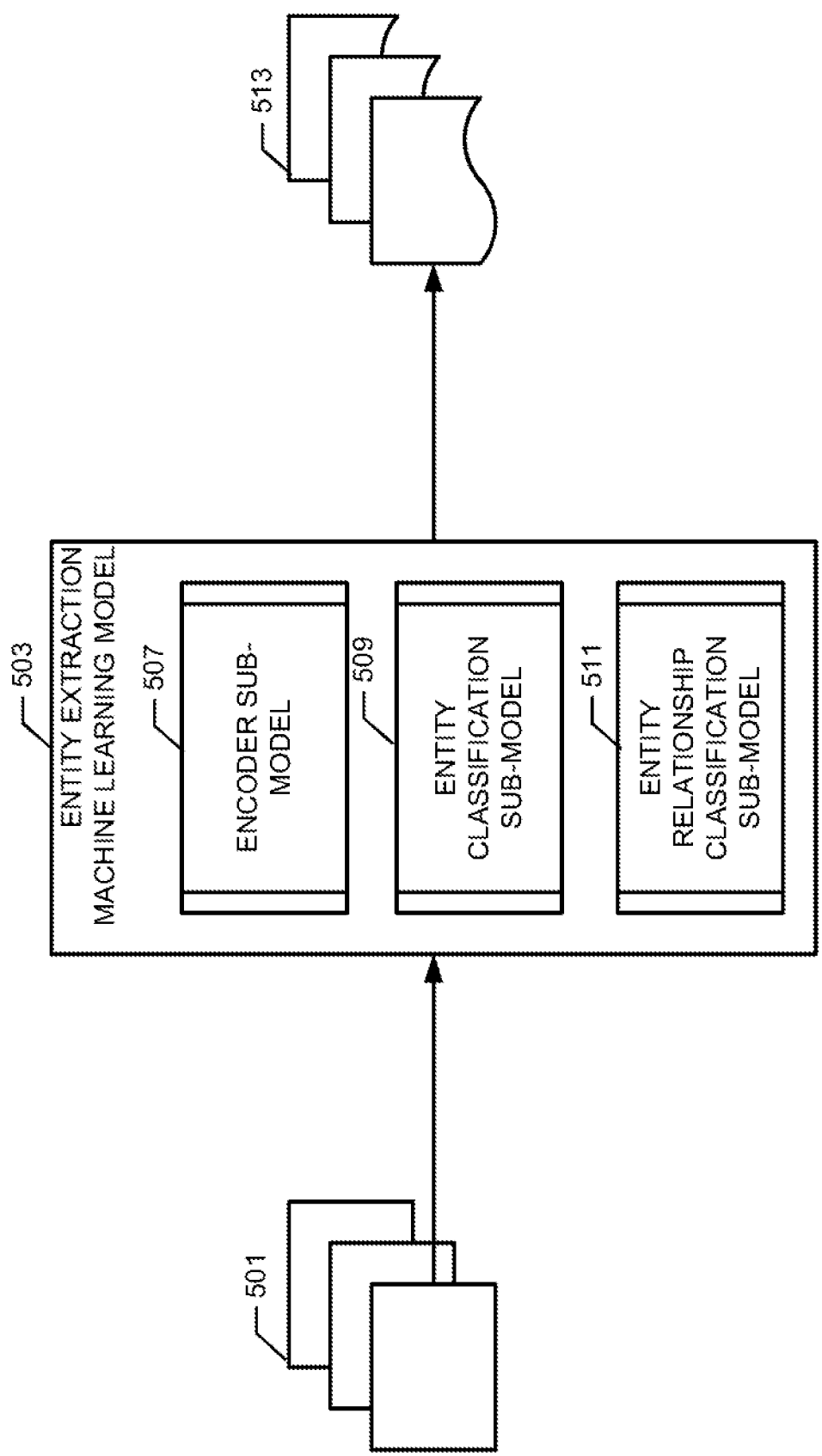

Referring now to FIG. 5, an example diagram illustrating example operations in accordance with various embodiments of the present disclosure is illustrated.

In the example shown in FIG. 5, a computing entity (such as the data object computing entity 105 described above in connection with FIG. 1 and FIG. 2) may include means (such as the processing element 205 of the data object computing entity 105 described above in connection with FIG. 2) to provide one or more natural language data objects 501 to an entity extraction machine learning model 503.

In some embodiments, the entity extraction machine learning model 503 is stored in a data object computing entity. In some embodiments, the entity extraction machine learning model 503 is stored in a computing entity that is different from the data object computing entity.

In some embodiments, the entity extraction machine learning model 503 generates one or more graph-based data objects 513 based at least in part on the one or more natural language data objects 501. In particular, FIG. 5 illustrates an example, multi-sub-model structure of the entity extraction machine learning model 503 that enables the entity extraction machine learning model 503 to achieve the function of generating the one or more graph-based data objects 513 based at least in part on the one or more natural language data objects 501.

In the example shown in FIG. 5, the entity extraction machine learning model 503 comprises an encoder sub-model 507, an entity classification sub-model 509, and an entity relationship classification sub-model 511. In some embodiments, two or more of the encoder sub-model 507, the entity classification sub-model 509, and the entity relationship classification sub-model 511 may be combined. In some embodiments, the encoder sub-model 507, the entity classification sub-model 509, and the entity relationship classification sub-model 511 are separate, different, and distinct sub-models of the entity extraction machine learning model 503.

Figure 6A:
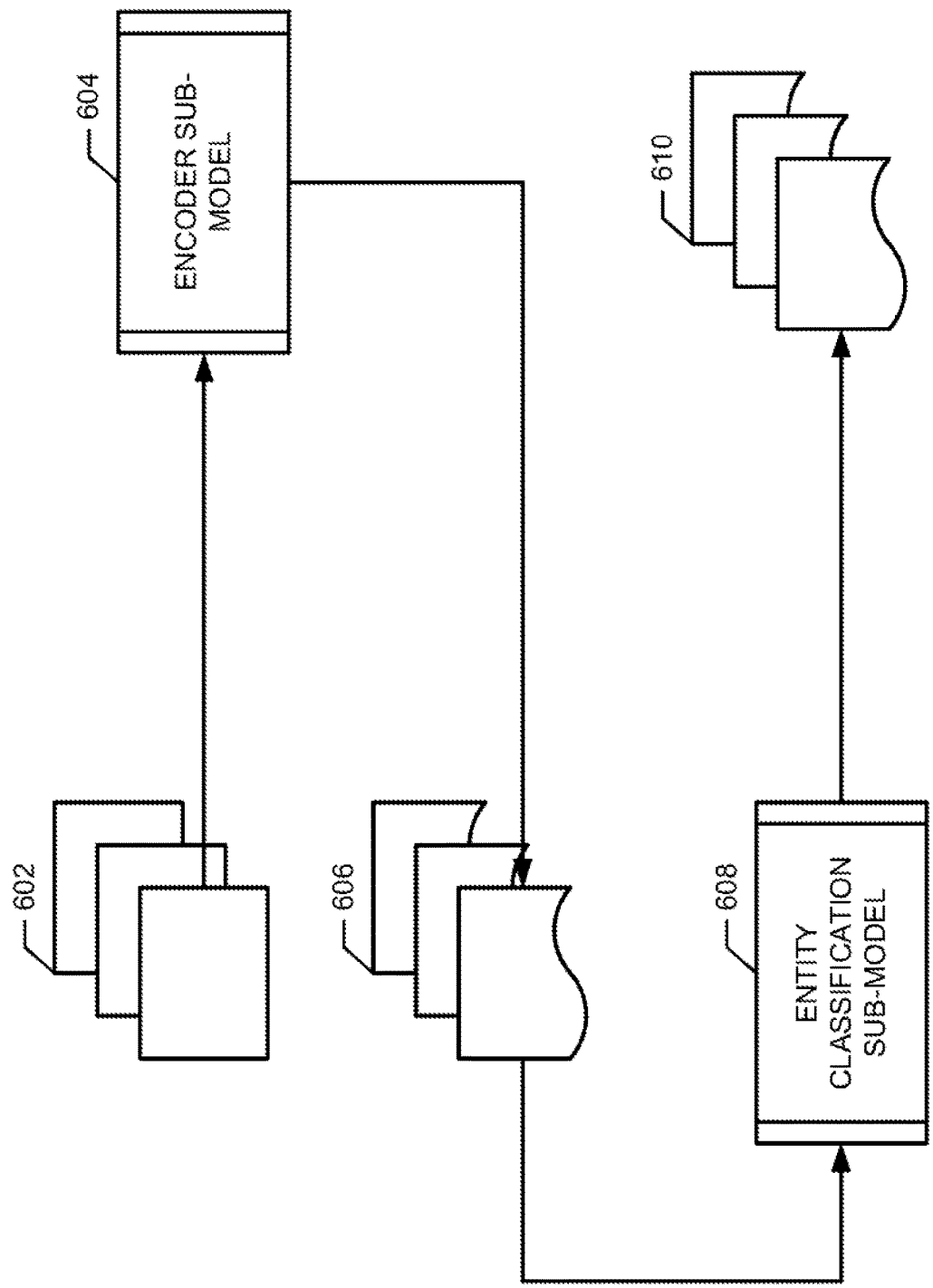

Referring now to FIG. 6A and FIG. 6B, example diagrams illustrating example data communications between various sub-models of an example entity extraction machine learning model is illustrated. In particular, FIG. 6A and FIG. 6B illustrate example data communications between an encoder sub-model 604, an entity classification sub-model 608, and an entity relationship classification sub-model 612 are illustrated.

Referring now to FIG. 6A, a plurality of natural language data objects 602 are provided as input data sets to the encoder sub-model 604. Based at least in part on the plurality of natural language data objects 602, the encoder sub-model 604 generates a plurality of text embeddings 606.

For example, the encoder sub-model 604 may generate the plurality of text embeddings 606 that are in the form of real-valued vectors that encode meanings of one or more words, one or more phrases, and/or one or more texts of the plurality of natural language data objects 602, similar to those described above in connection with at least step/operation 406 of FIG. 4.

Referring back to FIG. 6A, subsequent to the encoder sub-model 604 generating the plurality of text embeddings 606, the plurality of text embeddings 606 are provided to the entity classification sub-model 608 as input data sets. Based at least in part on the input data sets, the entity classification sub-model 608 generates a plurality of entity identifiers 610.

For example, the entity classification sub-model 608 may generate the plurality of entity identifiers 610 that each corresponds to an entity described in or associated with the plurality of natural language data objects 602. In some embodiments, the entity classification sub-model 608 may generate the plurality of entity identifiers 610 based at least in part on the plurality of text embeddings 606, similar to those described above in connection with at least step/operation 406 of FIG. 4.

In some embodiments, utilizing an entity classification sub-model to determine an entity classification and/or an entity identifier based at least in part on text embeddings generated by an encoder sub-model may provide various technical benefits and advantages. For example, as described above, the encoder sub-model may be associated with a multi-headed attention mechanism that provides natural language data objects to the attention layer of the encoder sub-model multiple times in parallel, therefore improving the speed in generating text embeddings and the accuracy level of text embeddings in representing meanings of word(s), phrase(s), and/or text(s) from the natural language data objects. By utilizing the text embeddings, the speed of the entity classification sub-model in determining the entity classifications from the natural language data objects, as well as the accuracies of the entity classifications determined by the entity classification sub-model, are improved in comparison to determining entity classifications directly from the natural language data objects and without utilizing the text embeddings.

Referring now to FIG. 6B, the entity relationship classification sub-model 612 utilizes the plurality of entity identifiers 610 generated by the entity classification sub-model 608 and the plurality of text embeddings 606 generated by the encoder sub-model 604 to generate a plurality of entity relationship identifiers 614.

For example, the entity relationship classification sub-model 612 may select two entity identifiers from the plurality of entity identifiers 610, determine a subset of text embeddings that correspond to these two entity identifiers from the plurality of text embeddings 606, and determine an entity relationship classification for these two entity identifiers based at least in part on the subset of text embeddings, similar to those described above in connection with at least step/operation 408 of FIG. 4.

In some embodiments, utilizing an entity relationship classification sub-model to determine an entity relationship classification and/or an entity relationship identifier based at least in part on text embeddings generated by an encoder sub-model may provide various technical benefits and advantages. For example, as described above, the encoder sub-model may be associated with a multi-headed attention mechanism that provides natural language data objects to the attention layer of the encoder sub-model multiple times in parallel, therefore improving the speed in generating text embeddings and the accuracy level of text embeddings in representing meanings of word(s), phrase(s), and/or text(s) from the natural language data objects. By utilizing the text embeddings, the speed of the entity relationship classification sub-model in determining the entity relationship classifications from the natural language data objects, as well as the accuracies of the entity relationship classifications determined by the entity classification sub-model, are improved in comparison to determining the entity relationship classifications directly from the natural language data objects and without utilizing the text embeddings.

Accordingly, as described above, various embodiments of the present invention improve computational efficiency of machine learning models. Data that comprises unformatted natural language (such as that found in contracts) does not yield very accurate predictions in machine learning environments at least due to their unformatted structure. In particular, machine learning models in many machine learning environments require that the input data to be formatted in such as a way that can be easily ingested by the machine learning models, and data that comprises unformatted natural language fails to meet this requirement and causes decline in the accuracy of outputs (such as predictions) generated by machine learning models. Accuracy of output of machine learning models is imperative in the many contexts, including, but not limited to, healthcare context. Various embodiments of the present disclosure overcome such technical limitations and deficiencies. For example, various embodiments of the present disclosure define a graph-based format for data that would improve the accuracy of predictions and/or decision determinations based at least in part on natural language documents (such as, but not limited to, contracts, medical records, and/or others) by machine learning models.

d. Exemplary Techniques For Generating Graph-Based Data Objects

As described above, there are technical challenges, deficiencies and problems associated with natural language processing and machine learning systems and methods, and various example embodiments of the present disclosure overcome such challenges. For example, referring now to FIG. 7, an example method 700 of generating an example graph-based data object in accordance with embodiments of the present disclosure is illustrated. For example, the example method 700 generates the graph-based data object based at least in part on the entity identifiers and entity relationship identifiers that are determined in accordance with various embodiments of the present disclosure. As such, the example method 700 overcomes various technical challenges.

Figure 7:
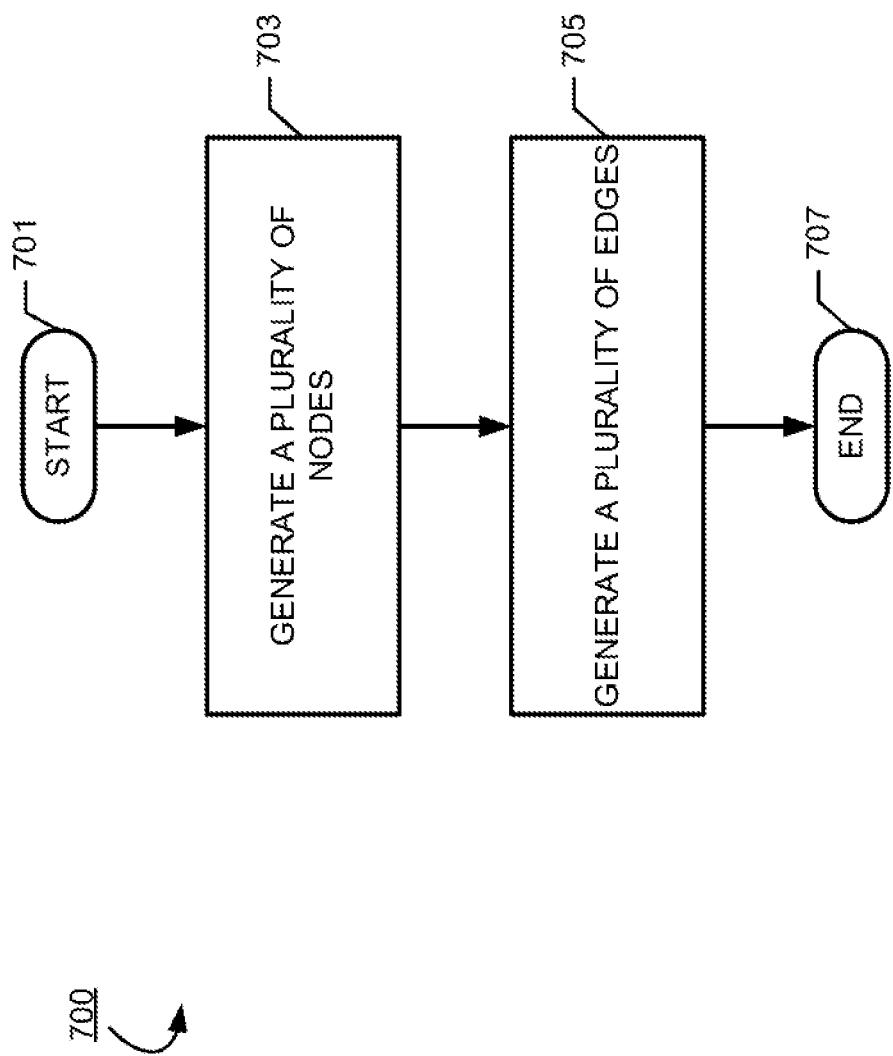

As shown in FIG. 7, the example method 700 starts at step/operation 701. Subsequent to and/or in response to step/operation 701, the example method 700 proceeds to step/operation 703. At step/operation 703, a computing entity (such as the data object computing entity 105 described above in connection with FIG. 1 and FIG. 2) may include means (such as the processing element 205 of the data object computing entity 105 described above in connection with FIG. 2) to generate a plurality of nodes.

In some embodiments, the processing element may utilize an entity classification sub-model to determine a plurality of entity identifiers from a plurality of natural language data objects based at least in part on text embeddings that are generated based at least in part on the plurality of natural language data objects, similar to those described above in connection with at least FIG. 4 to FIG. 6B. In some embodiments, the processing element may generate a node for each of the plurality of entity identifiers.

For example, the plurality of natural language data objects may include a medical record data object that describes a permanent knee damage symptom associated with a patient Adam. The plurality of natural language data objects may also include a textual contract data object that describes a procedure of knee replacement for the permanent knee damage symptom. In such an example, the processing element may utilize the encoder sub-model to generate text embeddings based at least in part on the medical record data object and the textual contract data object. The processing element may utilize the entity classification sub-model to determine entity identifiers that include "Adam" and "permanent knee damage" from text embeddings associated with the medical record data object, and determine entity identifiers that include "permanent knee damage" and "knee replacement" from text embeddings associated with the textual contract data object. In this example, the processing element may generate a node that represents "Adam," a node that represents "permanent knee damage," and a node that represents "knee replacement."

Referring back to FIG. 7, subsequent to and/or in response to step/operation 703, the example method 700 proceeds to step/operation 705. At step operation 705, a computing entity (such as the data object computing entity 105 described above in connection with FIG. 1 and FIG. 2) may include means (such as the processing element 205 of the data object computing entity 105 described above in connection with FIG. 2) to generate a plurality of edges.

In some embodiments, the processing element may utilize an entity relationship classification sub-model determine a plurality of entity relationship identifiers for each entity pair of entity identifiers based at least in part on a subset of text embeddings that are generated based at least in part on the plurality of natural language data objects and associated with the entity pair, similar to those described above in connection with at least FIG. 4 to FIG. 6B. In some embodiments, the processing element may generate the plurality of edges of the graph-based data object based at least in part on one or more entity relationship identifiers.

For example, when generating the plurality of edges, the processing element may further cause each of the plurality of edges to connect with at least two of the nodes generated at step/operation 703 based at least in part on the corresponding entity relationship identifier associated with these two nodes.

Continuing from the example above, the entity relationship classification determined for the entity pair of "Adam" and "permanent knee damage" may indicate that permanent knee damage is a symptom that Adam exhibits. As such, the processing element may generate an edge that connects the node that represents Adam with the node that represents permanent knee damage, and the edge type associated with the edge may indicate "exhibits." Additionally, the entity relationship classification determined for the entity pair of "knee replacement" and "permanent knee damage" may indicate that permanent knee damage is a prerequisite of knee replacement. As such, the processing element may generate an edge that connects the node that represents permanent knee damage with the node that represents knee replacement, and the edge type associated with the edge may indicate "prerequisite."

As shown in the above example, an example graph-based data object may connect data and/or information across different natural language data objects, and may facilitate generating prediction data for these natural language data objects, additional details of which are described herein.

Referring back to FIG. 7, subsequent to step/operation 705, the example method 700 proceeds to step/operation 707 and ends.

As described above, there are technical challenges, deficiencies and problems associated with natural language processing and machine learning systems and methods, and various example embodiments of the present disclosure overcome such challenges. For example, referring now to FIG. 8, an example method 800 of generating an example graph-based data object in accordance with embodiments of the present disclosure is illustrated. For example, the example method 800 determines that two or more natural language data objects (such as medical record data objects and textual contract data objects) are associated with a shared entity classification/identifier, and may generate a graph-based data object that connects data and/or information extracted from the two or more natural language data objects. As such, the example method 800 overcomes various technical challenges.

Figure 8:
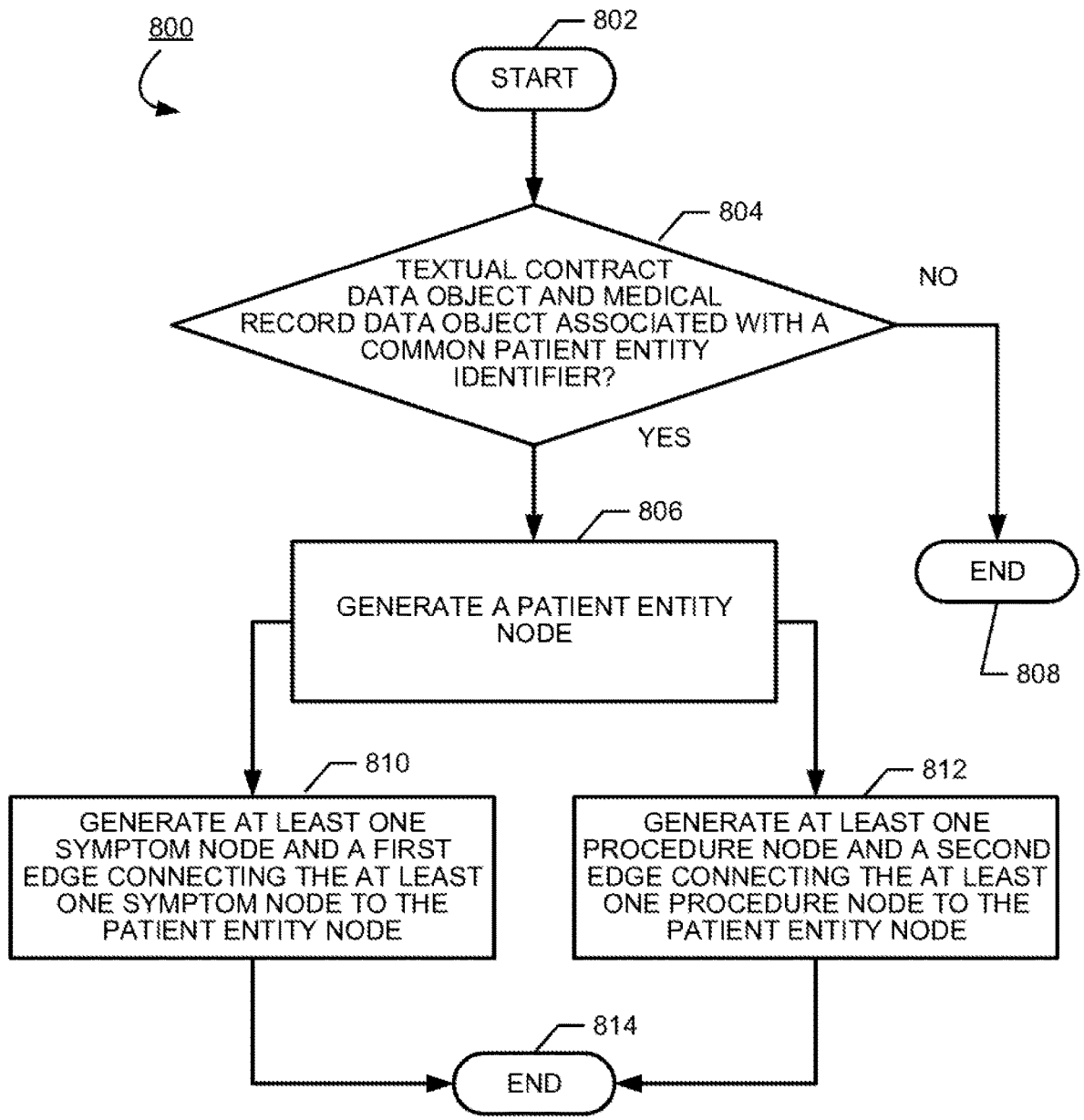

As shown in FIG. 8, the example method 800 starts at step/operation 802. Subsequent to and/or in response to step/operation 802, the example method 800 proceeds to step/operation 804. At step/operation 804, a computing entity (such as the data object computing entity 105 described above in connection with FIG. 1 and FIG. 2) may include means (such as the processing element 205 of the data object computing entity 105 described above in connection with FIG. 2) to determine whether a textual contract data object and a medical record data object are associated with at least one common entity classification or entity identifier (for example, the same patient entity identifier).

In some embodiments, the processing element may retrieve at least one natural language data object from a database, similar to those described above in connection with at least FIG. 4 to FIG. 6B above. In some embodiments, the plurality of natural language data objects comprises at least one textual contract data object and at least one medical record data object.

In some embodiments, the processing element may determine one or more entity identifiers from at least one textual contract data object and at least one medical record data object. For example, the processing element may determine the plurality of entity identifiers by utilizing an entity extraction machine learning model that comprises an encoder sub-model and an entity classification sub-model. In some embodiments, the encoder sub-model is configured to generate a plurality of text embeddings based at least in part on the plurality of natural language data objects, and the entity classification sub-model is configured to determine an entity classification for each text embedding, similar to those described above in connection with at least FIG. 4 to FIG. 6B. In some embodiments, the processing element may determine an entity identifier based at least in part on the entity classification, similar to those described above in connection with at least FIG. 4 to FIG. 6B.

In some embodiments, the processing element may determine whether at least one textual contract data object and at least one medical record data object share one or more common entity identifiers or entity classifications. In some embodiments, the processing element may determine whether at least one textual contract data object and at least one medical record data object are associated with at least one common patient entity identifier (also referred to as a first patient entity identifier herein in connection with the description of FIG. 8) that corresponds to a patient.

Referring back to FIG. 8, if, at step/operation 804, the processing element determines that either one of the textual contract data object or the medical record data object is not associated with a first patient entity identifier (e.g. the textual contract data object and the medical record data object are not associated with a common patient entity identifier), the example method 800 proceeds to step/operation 808 and ends.

For example, in response to determining that either one of the textual contract data object or the medical record data object is not associated with a first patient entity identifier, the processing element determines that the textual contract data object and the medical record data object are not associated with the same patient, and the example method 800 ends.

Additionally, or alternatively, in response to determining that either one of the textual contract data object or the medical record data object is not associated with a first patient entity identifier, the processing element may generate multiple graph-based data objects. For example, if the textual contract data object is associated with the first patient entity identifier and the medical record data object is associated with a second patient entity identifier, the processing element may generate a first graph-based data object based at least in part on the textual contract data object, and may generate a second graph-based data object based at least in part on the medical record data object. In some embodiments, there may not be a connection between the first graph-based data object and the second graph-based data object.

Referring back to FIG. 8, if at step/operation 804, the processing element determines that both the textual contract data object and the medical record data object are associated with the common patient entity identifier, the example method 800 proceeds to step/operation 806. At step/operation 806, a computing entity (such as the data object computing entity 105 described above in connection with FIG. 1 and FIG. 2) may include means (such as the processing element 205 of the data object computing entity 105 described above in connection with FIG. 2) to generate a patient entity node.

In some embodiments, the processing element generates a patient entity node that indicates, represents, and/or corresponds to the common patient entity identifier (e.g. the first patient entity identifier) in response to determining that the first patient entity identifier is shared between at least one textual contract data object and the at least one medical record data object.

In such an example, both the at least one textual contract data object and the at least one medical record data object of step/operation 804 are associated with the same patient. For example, the at least one medical record data object may comprise data and/or information associated with a medical record of the patient, and the at least one textual contract data object may comprise data and/or information associated with an insurance agreement between the patient and a health insurance provider.

Figure 9:
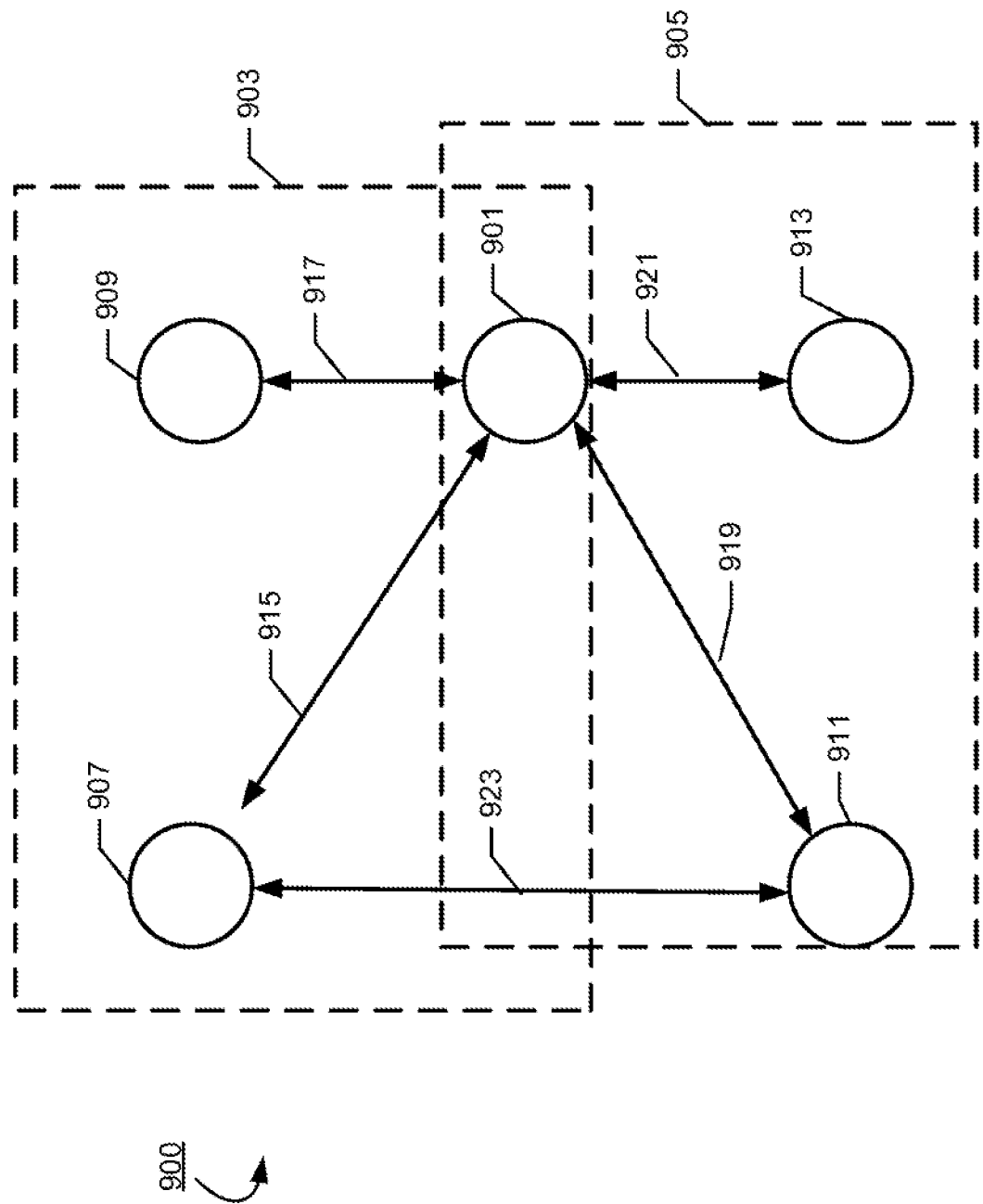

For example, referring now to FIG. 9, an example patient entity node 901 is illustrated. In this example, the example patient entity node 901 may be associated with both a medical record data object and a textual contract data object. In the example shown FIG. 9, the dashed box 903 indicates that the example patient entity node 901 is associated with the medical record data object, and the dashed box 905 indicates that the example patient entity node 901 is associated with the textual contract data object.

Referring back to FIG. 8, subsequent to and/or in response to step/operation 806, the example method 800 proceeds to step/operation 810. At step/operation 810, a computing entity (such as the data object computing entity 105 described above in connection with FIG. 1 and FIG. 2) may include means (such as the processing element 205 of the data object computing entity 105 described above in connection with FIG. 2) to generate at least one symptom node and a first edge connecting the at least one symptom node to the patient entity node.

In some embodiments, the processing element may generate at least one symptom node and a first edge connecting the at least one symptom node to the patient entity node based at least in part on the at least one medical record data object described above in connection with at least step/operation 804.

For example, the processing element may utilize an entity extraction machine learning model that comprises an encoder sub-model and an entity classification sub-model. Similar to those described above in connection with at least FIG. 4 to FIG. 7, the encoder sub-model is configured to generate a plurality of text embeddings based at least in part on the at least one medical record data object, and the entity classification sub-model is configured to determine an entity classification for each text embedding. In some embodiments, the entity classification sub-model may determine at least one entity classification that corresponds to at least one symptom, and the processing element may determine at least one symptom identifier based at least in part on the at least one entity classification, and may generate at least one node that corresponds to the at least one symptom identifier.

Additionally, in some embodiments, the entity extraction machine learning model may comprise an entity relationship classification sub-model. Similar to those described above in connection with at least FIG. 4 to FIG. 7, the entity relationship classification sub-model is configured to determine an entity relationship classification for each entity pair (e.g. two entity identifiers) from the plurality of entity identifiers. For example, the entity relationship classification sub-model may determine at least one entity relationship classification between the patient entity identifier associated with the patient entity node generated at step/operation 806 and at least one symptom identifier associated with the at least one symptom node generated at step/operation 810. The processing element may generate at least entity relationship identifier based at least in part on the at least one entity relationship classification, and may generate an edge that connects the patient entity node and the at least one symptom node based at least in part on the at least one entity relationship identifier.

Referring now to FIG. 9, the processing element may generate a first symptom node 907 and a second symptom node 909 based at least in part on symptom identifiers that are determined in accordance with various examples described herein. The processing element may generate an edge 915 that connects the first symptom node 907 to the patient entity node 901, and an edge 917 that connects the second symptom node 909 to the patient entity node 901 based at least in part on the entity relationship identifies that are determined in accordance with various examples described herein. For example, the edge 915 may indicate that the patient represented by the patient entity node 901 exhibits the symptom represented by the first symptom node 907, and the edge 917 may indicate that the patient represented by the patient entity node 901 exhibits the symptom represented by the second symptom node 909. In the example shown in FIG. 9, the dashed box 903 indicates that the patient entity node 901, the first symptom node 907 and the second symptom node 909 are all associated with the same medical record data object.

Referring back to FIG. 8, subsequent to and/or in response to step/operation 806, the example method 800 proceeds to step/operation 812. At step/operation 812, a computing entity (such as the data object computing entity 105 described above in connection with FIG. 1 and FIG. 2) may include means (such as the processing element 205 of the data object computing entity 105 described above in connection with FIG. 2) to generate at least one procedure node and a second edge connecting the at least one procedure node to the patient entity node.

In some embodiments, the processing element may generate at least one procedure node and a second edge connecting the at least one procedure node to the patient entity node based at least in part on the at least one textual contract data object described above in connection with at least step/operation 804.

For example, the processing element may utilize an entity extraction machine learning model that comprises an encoder sub-model and an entity classification sub-model. Similar to those described above in connection with at least FIG. 4 to FIG. 7, the encoder sub-model is configured to generate a plurality of text embeddings based at least in part on the at least one textual contract data object, and the entity classification sub-model is configured to determine an entity classification for each text embedding. In some embodiments, the entity classification sub-model may determine at least one entity classification that corresponds to at least one procedure, and the processing element may determine at least one procedure identifier based at least in part on the at least one entity classification, and may generate at least one node that corresponds to the at least one procedure identifier.

Additionally, in some embodiments, the entity extraction machine learning model may comprise an entity relationship classification sub-model. Similar to those described above in connection with at least FIG. 4 to FIG. 7, the entity relationship classification sub-model is configured to determine an entity relationship classification for each entity pair (e.g. two entity identifiers) from the plurality of entity identifiers. For example, the entity relationship classification sub-model may determine at least one entity relationship classification between the patient entity identifier associated with the patient entity node generated at step/operation 806 and at least one procedure identifier associated with the at least one procedure node generated at step/operation 812. The processing element may generate at least entity relationship identifier based at least in part on the at least one entity relationship classification, and may generate an edge that connects the patient entity node and the at least one procedure node based at least in part on the at least one entity relationship identifier.

Referring now to FIG. 9, the processing element may generate a first procedure node 911 and a second procedure node 913 based at least in part on procedure identifiers that are determined in accordance with various examples described herein. In the example shown in FIG. 9, the dashed box 905 indicates that the patient entity node 901, the first procedure node 911 and the second procedure node 913 are all associated with the same textual contract data object.

In some embodiments, the processing element may generate an edge 919 that connects the first procedure node 911 to the patient entity node 901, and an edge 921 that connects the second procedure node 913 to the patient entity node 901 based at least in part on the entity relationship identifies that are determined in accordance with various examples described herein.

For example, the textual contract data object may be associated with a health insurance agreement between the patient represented by the patient entity node 901 and a health insurance provider. The edge 919 may indicate that the procedure represented by the first procedure node 911 is covered by the health insurance agreement of the patient represented by the patient entity node 901, and the edge 921 may indicate that the procedure represented by the second procedure node 913 is covered by the health insurance agreement of the patient represented by the patient entity node 901.

In some embodiments, the at least one procedure node is associated with at least one international Classification of Diseases (ICD) code. For example, the at least one procedure node may indicate, describe, and/or represent one or more medical procedures for treating one or more diseases as indicated by the ICD codes.

In some embodiments, the processing element may generate one or more edges connecting one or more nodes that are generated based at least in part on entity identifiers determined from different natural language data objects. In the example shown in FIG. 9, the processing element may utilize an entity relationship classification sub-model based at least in part on text embeddings from the at least one medical record data object and the at least one textual contract data object, and may determine an entity relationship identifier associated with the symptom identifier corresponding to the first symptom node 907 and the procedure identifier corresponding to the first procedure node 911. For example, the processing element may determine that the first procedure node 911 is associated with a procedure for treating the symptom associated with the first symptom node 907. Accordingly, the processing element may generate an edge 923 that connects the first procedure node 911 and the first symptom node 907 based at least in part on the determined entity relationship identifier.

As illustrated in the example of FIG. 9, the graph-based data object 900 comprises a plurality of nodes (such as, but not limited to, a patient entity node 901, a first symptom node 907, a second symptom node 909, a first procedure node 911, and a second procedure node 913) and a plurality of edges (such as, but not limited to, the edge 915, the edge 917, the edge 919, the edge 921, and the edge 923) connecting the plurality of nodes. In some embodiments, the plurality of nodes is associated with a plurality of node types, and the plurality of edges is associated with a plurality of edge types based at least in part on the plurality of node types. For example, each of the plurality of nodes corresponds to an entity or a concept associated with the plurality of natural language data objects (for example, a patient entity, a symptom, a procedure, and/or the like). Each of the plurality of edges corresponds to a relationship between entities or concepts associated with the plurality of natural language data objects (for example, a patient exhibits a particular symptom, a particular medical procedure has been preauthorized for treating the particular symptom, and/or the like).

Referring back to FIG. 8, subsequent to and/or in response to step/operation 810 and/or step/operation 812, the example method 800 proceeds to step/operation 814 and ends.

e. Exemplary Techniques For Performing Prediction-Based Actions

As described above, there are technical challenges, deficiencies and problems associated with natural language processing and machine learning systems and methods, and various example embodiments of the present disclosure overcome such challenges. For example, referring now to FIG. 10, an example method 1000 of performing prediction-based actions based at least in part on a graph-based data object in accordance with embodiments of the present disclosure is illustrated. For example, the example method 1000 identifies a related sub-graph of the graph-based data object and generates at least one prediction data object based at least in part on the related sub-graph and using a data prediction machine learning model, details of which are described herein. As such, the example method 1000 overcomes various technical challenges.

Figure 10:
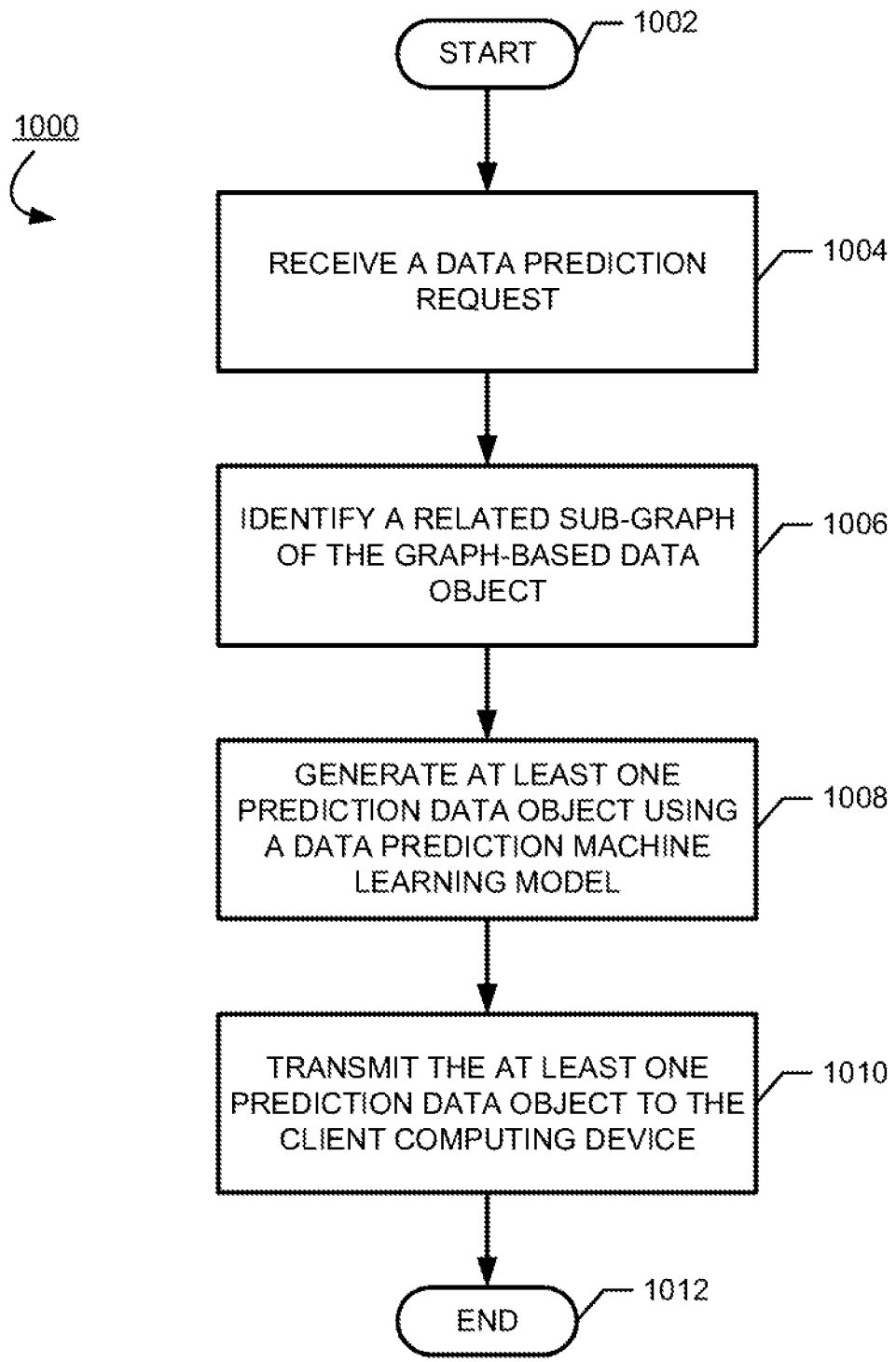

As shown in FIG. 10, the example method 1000 starts at step/operation 1002. Subsequent to and/or in response to step/operation 1002, the example method 1000 proceeds to step/operation 1004. At step/operation 1004, a computing entity (such as the data object computing entity 105 described above in connection with FIG. 1 and FIG. 2) may include means (such as the processing element 205 of the data object computing entity 105 described above in connection with FIG. 2) to receive a data prediction request.

In some embodiments, the processing element receives a data prediction request from a client computing device. In some embodiments, the data prediction request is associated with at least one entity identifier from a plurality of entity identifiers as determined from at least one natural language data object in accordance with various examples described above. For example, the data prediction request may comprise an electronic request to generate one or more data predictions associated with an entity as indicated by the entity identifier.

As an example, the data prediction request may comprise an electronic request to generate a data prediction on whether a medical procedure can be preauthorized for a patient John. In this example, the data prediction request is associated with both a procedure identifier and a patient entity identifier.

Referring back to FIG. 10, subsequent to and/or in response to step/operation 1004, the example method 1000 proceeds to step/operation 1006. At step/operation 1006, a computing entity (such as the data object computing entity 105 described above in connection with FIG. 1 and FIG. 2) may include means (such as the processing element 205 of the data object computing entity 105 described above in connection with FIG. 2) to identify a related sub-graph of the graph-based data object.

In some embodiments, the processing element may identify, based at least in part on the at least one entity identifier associated with the data prediction request received at step/operation 1004, a related sub-graph of the graph-based data object that corresponds to the at least one entity identifier in response to receiving the data prediction request at step/operation 1004.

Continuing from the example above, based at least in part on the at least one entity identifier comprising a patient entity identifier of John, the processing element may determine a patient entity node corresponding to the patient entity identifier that represents John from the graph-based data object. In some embodiments, the processing element may further determine one or more additional nodes that are connected to the patient entity node via one or more edges, and may determine that these additional nodes, along with the patient entity node, are part of related sub-graph that corresponds to the patient entity identifier of John.

Referring back to FIG. 10, subsequent to and/or in response to step/operation 1006, the example method 1000 proceeds to step/operation 1008. At step/operation 1008, a computing entity (such as the data object computing entity 105 described above in connection with FIG. 1 and FIG. 2) may include means (such as the processing element 205 of the data object computing entity 105 described above in connection with FIG. 2) to generate at least one prediction data object using a data prediction machine learning model.

In some embodiments, the processing element may generate at least one prediction data object using a data prediction machine learning model based at least in part on the related sub-graph identified at step/operation 1006.

For example, the processing element may provide the related sub-graph to the data prediction machine learning model as input data sets. As described above, the data prediction machine learning model may be trained to generate at least one prediction data object based at least in part on the sub-graph of the graph-based data object. Additional details associated with training the prediction machine learning model are described herein, including, but not limited to, those described in connection with at least FIG. 12.

Referring back to FIG. 10, subsequent to and/or in response to step/operation 1008, the example method 1000 proceeds to step/operation 1010. At step/operation 1010, a computing entity (such as the data object computing entity 105 described above in connection with FIG. 1 and FIG. 2) may include means (such as the processing element 205 of the data object computing entity 105 described above in connection with FIG. 2) to transmit the at least one prediction data object to the client computing device.

In some embodiments, the processing element may transmit the at least one prediction data object to the same client computing device from which the data prediction request was received at step/operation 1004.

Referring back to FIG. 10, subsequent to step/operation 1010, the example method 1000 proceeds to step/operation 1012 and ends.

As described above, there are technical challenges, deficiencies and problems associated with natural language processing and machine learning systems and methods, and various example embodiments of the present disclosure overcome such challenges. For example, referring now to FIG. 11, an example method 1100 of generating at least one prediction data object in accordance with embodiments of the present disclosure is illustrated. As such, the example method 1100 overcomes various technical challenges.

For example, the example method 1100 determines a first node of a graph-based data object that is associated with an entity identifier, determines at least an edge that connects the first node to a second node, and generates at least one prediction data object based at least in part on the first node, the first edge, and the second node.

Figure 11:
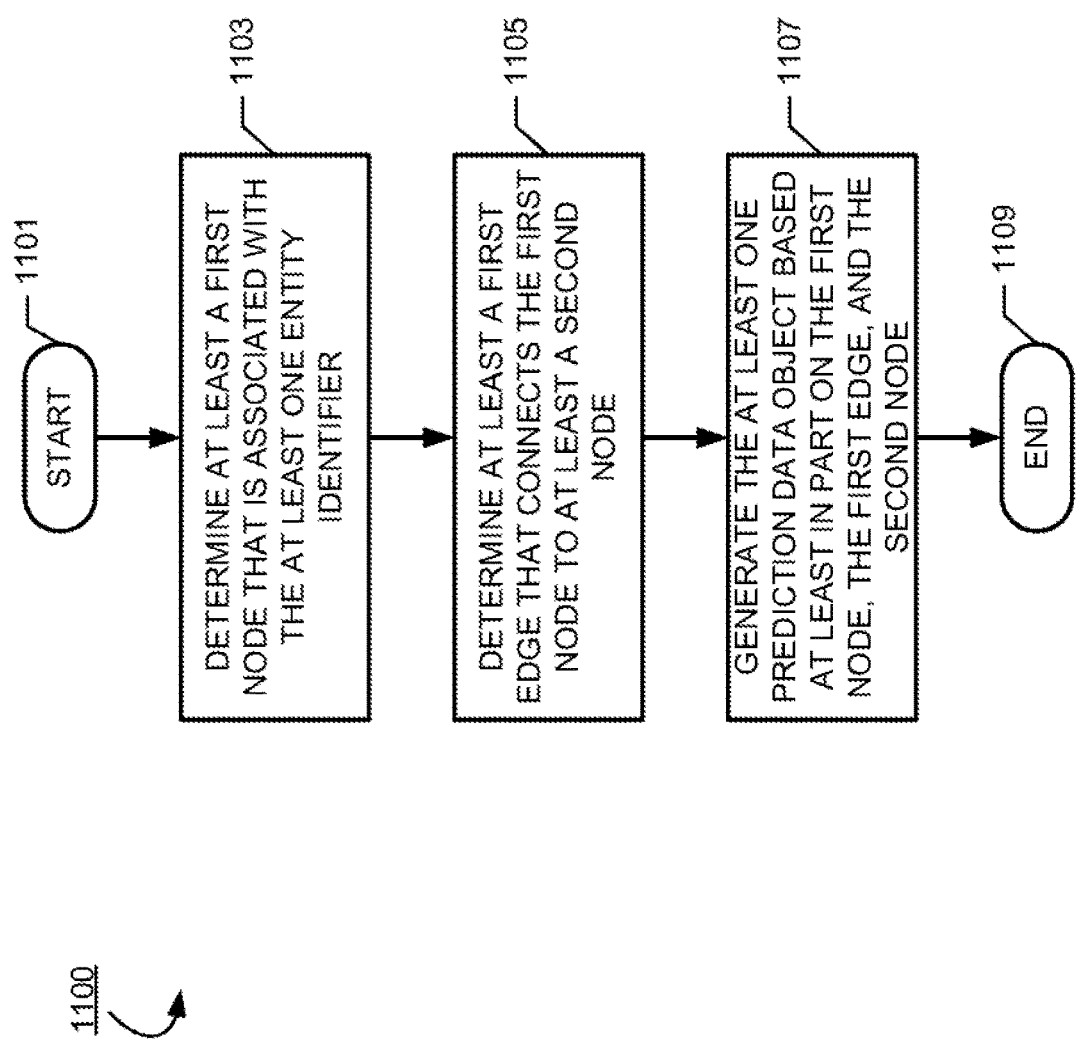

As shown in FIG. 11, the example method 1100 starts at step/operation 1101. Subsequent to and/or in response to step/operation 1101, the example method 1100 proceeds to step/operation 1103. At step/operation 1103, a computing entity (such as the data object computing entity 105 described above in connection with FIG. 1 and FIG. 2) may include means (such as the processing element 205 of the data object computing entity 105 described above in connection with FIG. 2) to determine at least a first node that is associated with the at least one entity identifier.

In some embodiments, the step/operation 1103 and step/operation 1105 may be part of identifying the related sub-graph of a graph-based data object in connection with at least step/operation 1006 of FIG. 10.

For example, the processing element may receive an electronic request (such as, but not limited to, a data prediction request) from a client computing entity, and the electronic request may be associated with or indicate at least one entity identifier. In some embodiments, the processing element may determine at least a first node from a plurality of nodes of the graph-based data object that is associated with at least one entity identifier.

Referring back to FIG. 11, subsequent to and/or in response to step/operation 1103, the example method 1100 proceeds to step/operation 1105. At step/operation 1105, a computing entity (such as the data object computing entity 105 described above in connection with FIG. 1 and FIG. 2) may include means (such as the processing element 205 of the data object computing entity 105 described above in connection with FIG. 2) to determine at least a first edge that connects the first node determined at step/operation 1103 to at least a second node.

As described above, an example graph-based data object may comprise one or more edges connecting one or more nodes. Each of the one or more edges may be generated based at least in part on an entity relationship identifier that indicates an entity relationship between the nodes.

In some embodiments, the processing element may determine at least a first edge from a plurality of edges of the graph-based data object that connects the first node determined at step/operation 1103 to at least a second node.

Referring back to FIG. 11, subsequent to and/or in response to step/operation 1105, the example method 1100 proceeds to step/operation 1107. At step/operation 1107, a computing entity (such as the data object computing entity 105 described above in connection with FIG. 1 and FIG. 2) may include means (such as the processing element 205 of the data object computing entity 105 described above in connection with FIG. 2) to generate at least one prediction data object based at least in part on the first node, the first edge, and the second node.

In some embodiments, the processing element may generate at least one prediction data object based at least in part on the first node, the first edge, and the second node as a related sub-graph of the graph-based data object. The processing element may provide the related sub-graph that comprises the first node, the first edge, and the second node to a data prediction machine learning model. As described above, the data prediction machine learning model may be trained to generate at least one prediction data object based at least in part on the sub-graph of the graph-based data object. As such, the data prediction machine learning model may generate a prediction data object based at least in part on the first node, the first edge, and the second node.

Referring back to FIG. 11, subsequent to step/operation 1107, the example method 1100 proceeds to step/operation 1109 and ends.

As described above, there are technical challenges, deficiencies and problems associated with natural language processing and machine learning systems and methods, and various example embodiments of the present disclosure overcome such challenges. For example, referring now to FIG. 12, an example method 1200 of generating one or more prediction data objects based at least in part on training a supervised machine learning model in accordance with embodiments of the present disclosure is illustrated. For example, the example method 1200 trains a data prediction machine learning model using a training data set, and generates at least one prediction data object based at least in part on a graph-based data object and the trained data prediction machine learning model. As such, the example method 1200 overcomes various technical challenges.

Figure 12:
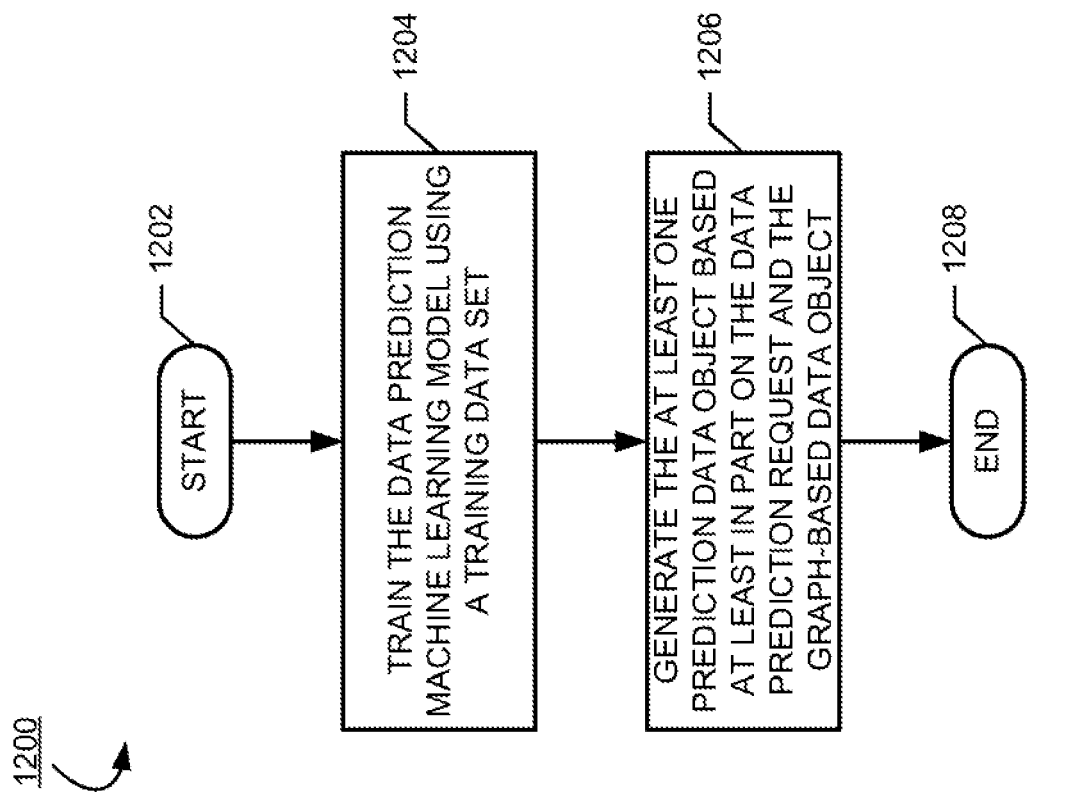

As shown in FIG. 12, the example method 1200 starts at step/operation 1202. Subsequent to and/or in response to step/operation 1202, the example method 1200 proceeds to step/operation 1204. At step/operation 1204, a computing entity (such as the data object computing entity 105 described above in connection with FIG. 1 and FIG. 2) may include means (such as the processing element 205 of the data object computing entity 105 described above in connection with FIG. 2) to train the data prediction machine learning model using a training data set.

In some embodiments, the training data set comprises a plurality of historical data prediction requests and a plurality of historical response data objects. In particular, the plurality of historical data prediction requests is associated with one or more natural language data objects and/or on one or more graph-based data objects that are generated based at least in part on the one or more natural language data objects. Each of the historical response data objects indicates, represents, and/or describes a response or an outcome to a historical data prediction request.

As an example, the plurality of historical data prediction requests may be associated with a plurality of preauthorization requests, and the plurality of historical response data objects may each indicate whether a preauthorization request of the plurality of preauthorization requests was approved.

In some embodiments, to train the data prediction machine learning model, the processing element may generate at least one graph-based data object in accordance with various examples described herein. For example, the plurality of historical data prediction requests may be associated with a plurality of natural language data objects, and the processing element generates at least one graph-based data object based at least in part on the plurality of natural language data objects. The processing element may provide the at least one graph-based data object and the plurality of historical data prediction requests to the data prediction machine learning model, and the data prediction machine learning model may generate a plurality of prediction data objects in response to the plurality of historical data prediction requests and based at least in part on the at least one graph-based data object. In some embodiments, the processing element may cause the prediction machine learning model to compare the plurality of prediction data objects with the plurality of historical response data objects, and cause the prediction machine learning model to adjust one or more of its parameters so as to generate prediction data objects that match or are close to the corresponding historical response data objects. As such, through training, the accuracy of the data prediction machine learning model in generating prediction data objects can be improved.

Referring back to FIG. 12, subsequent to and/or in response to step/operation 1204, the example method 1200 proceeds to step/operation 1206. At step operation 1206, a computing entity (such as the data object computing entity 105 described above in connection with FIG. 1 and FIG. 2) may include means (such as the processing element 205 of the data object computing entity 105 described above in connection with FIG. 2) to generate at least one prediction data object based at least in part on the data prediction request and the graph-based data object.

In some embodiments, subsequent to training the data prediction machine learning model, the processing element may receive a data prediction request. In some embodiments, the processing element may generate at least one prediction data object based at least in part on the data prediction request and at least one graph-based data object generated in accordance with various examples provided herein.

Referring back to FIG. 12, subsequent to step/operation 1206, the example method 1200 proceeds to step/operation 1208 and ends.

As described above, there are technical challenges, deficiencies and problems associated with natural language processing and machine learning systems and methods, and various example embodiments of the present disclosure overcome such challenges. For example, referring now to FIG. 13, an example method 1300 of calculating a prediction confidence score in accordance with embodiments of the present disclosure is illustrated.

For example, the example method 1300 identifies a patient entity node, a healthcare provider entity node, and a procedure node in response to receiving a data prediction request that is associated with a preauthorization request, and programmatically calculates a prediction confidence score that indicates a predicted likelihood of approving the preauthorization request. As such, the example method 1300 overcomes various technical challenges.

Figure 13:
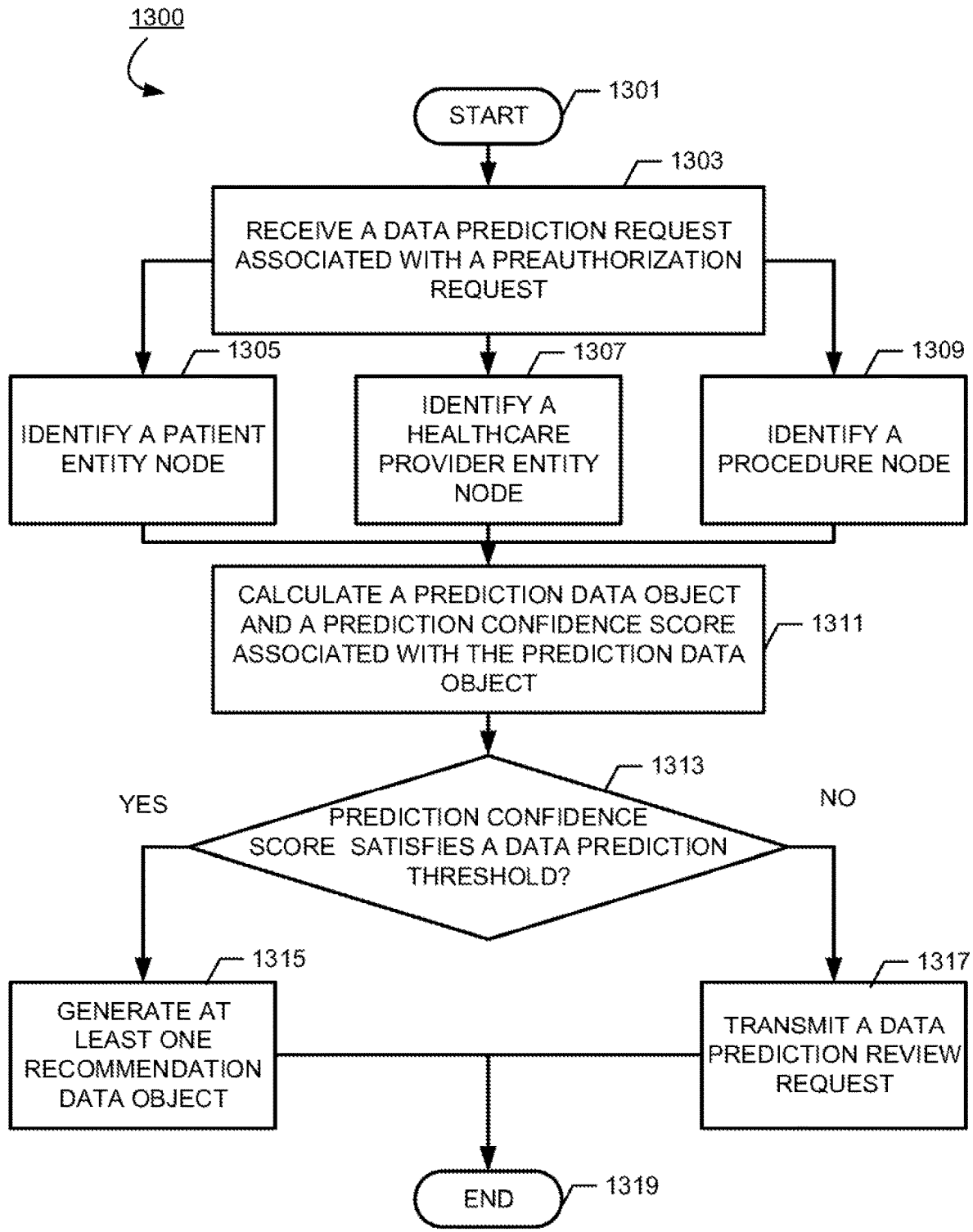

As shown in FIG. 13, the example method 1300 starts at step/operation 1301. Subsequent to and/or in response to step/operation 1301, the example method 1300 proceeds to step/operation 1303. At step/operation 1303, a computing entity (such as the data object computing entity 105 described above in connection with FIG. 1 and FIG. 2) may include means (such as the processing element 205 of the data object computing entity 105 described above in connection with FIG. 2) to receive a data prediction request that is associated with a preauthorization request.

As described above, an example preauthorization request may comprise a request to a health insurance provider to approve one or more medical procedures, one or more medical tests, one or more medications, and/or the like that are to be provided to or rendered on a patient by a healthcare provider. The data prediction request associated with the preauthorization request may indicate/comprise an electronic request to predict or estimate whether the preauthorization request will be or should be approved by the health insurance provider, and/or the likelihood that the health insurance provider will or should approve the preauthorization request.

In some embodiments, the data prediction request associated with the preauthorization request may comprise a procedure identifier, a patient entity identifier, and a healthcare provider entity identifier. For example, the procedure identifier may correspond to a medical procedure for which the healthcare provider is seeking approval through the preauthorization request. The patient entity identifier may correspond to a patient that the medical procedure is to be rendered on. The healthcare provider entity identifier corresponds to the healthcare provider who will render or conduct the procedure on the patient.

Referring back to FIG. 13, subsequent to and/or in response to step/operation 1303, the example method 1300 proceeds to step/operation 1305. At step/operation 1305, a computing entity (such as the data object computing entity 105 described above in connection with FIG. 1 and FIG. 2) may include means (such as the processing element 205 of the data object computing entity 105 described above in connection with FIG. 2) to identify a patient entity node.

As described above, in some embodiments, the processing element may generate at least one graph-based data object based at least in part on at least one natural language data object. In some embodiments, the at least one graph-based data object comprises a plurality of nodes. In some embodiments, the processing element may identify a patient entity node from a plurality of nodes of the graph-based data object based at least in part on the patient entity identifier associated with the preauthorization request as described above in connection with step/operation 1303.

Referring back to FIG. 13, subsequent to and/or in response to step/operation 1303, the example method 1300 proceeds to step/operation 1307. At step/operation 1307, a computing entity (such as the data object computing entity 105 described above in connection with FIG. 1 and FIG. 2) may include means (such as the processing element 205 of the data object computing entity 105 described above in connection with FIG. 2) to identify a healthcare provider entity node.

In some embodiments, the processing element may identify a healthcare provider entity node from the plurality of nodes of the graph-based data object based at least in part on the healthcare provider entity identifier associated with the preauthorization request as described above in connection with step/operation 1303.

Referring back to FIG. 13, subsequent to and/or in response to step/operation 1303, the example method 1300 proceeds to step/operation 1309. At step/operation 1309, a computing entity (such as the data object computing entity 105 described above in connection with FIG. 1 and FIG. 2) may include means (such as the processing element 205 of the data object computing entity 105 described above in connection with FIG. 2) to identify a procedure node.

In some embodiments, the processing element may identify a procedure node from the plurality anodes of the graph-based data object based at least in part on the procedure identifier associated with the preauthorization request as described above in connection with step/operation 1303.

Referring back to FIG. 13, subsequent to and/or in response to step/operation 1305, step/operation 1307, and/or step/operation 1309, the example method 1300 proceeds to step/operation 1311. At step/operation 1311, a computing entity (such as the data object computing entity 105 described above in connection with FIG. 1 and FIG. 2) may include means (such as the processing element 205 of the data object computing entity 105 described above in connection with FIG. 2) to calculate a prediction data object and a prediction confidence score associated with the prediction data object.

In some embodiments, the prediction data object indicates a predicted probability of at least one edge connecting the procedure node to the patient entity node and to the healthcare provider entity node.

If there is predicted to be at least one edge connecting the procedure node to the patient entity node and there is predicted to be at least one edge connecting the procedure node to the healthcare provider entity node, then the prediction data object indicates that the procedure represented by the procedure node should be preauthorized for the healthcare provider represented by the healthcare provider entity node to render on the patient represented by the patient entity node.

If there is predicted to be no edge connecting the procedure node to the patient entity node and/or there is predicted to be no edge connecting the procedure node to the healthcare provider entity node, then the prediction data object indicates that the procedure represented by the procedure node should not be preauthorized for the healthcare provider represented by the healthcare provider entity node to render on the patient represented by the patient entity node In some embodiments, the processing element may provide a related sub-graph of the graph-based data object that includes the patient entity node identified at step/operation 1305, the healthcare provider entity node identified at step/operation 1307, and/or the procedure node identified at step/operation 1309 to a data prediction machine learning model. The data prediction machine learning model may generate the prediction data object indicating the likelihood that there is at least one edge connecting the procedure node to the patient entity node and that there is at least one edge connecting the procedure node and the healthcare provider entity node.

In some embodiments, the data prediction machine learning model is an unsupervised machine learning model that is not trained through supervised learning. In some embodiments, the data prediction machine learning model is a supervised machine learning model. For example, the data prediction machine learning model has been trained using a training data set in accordance with at least FIG. 12 described above.

Additionally, the processing element may calculate a prediction confidence score associated with the prediction data object. As described above, the prediction confidence score confidence level or likelihood associated with the predicted or estimated outcome that is represented by, is indicated by, and/or is associated with a prediction data object.

Referring back to FIG. 13, subsequent to and/or in response to step/operation 1311, the example method 1300 proceeds to step/operation 1313. At step/operation 1313, a computing entity (such as the data object computing entity 105 described above in connection with FIG. 1 and FIG. 2) may include means (such as the processing element 205 of the data object computing entity 105 described above in connection with FIG. 2) to determine whether the prediction confidence score satisfies a data prediction threshold.

As described above, a data prediction threshold may indicate a baseline confidence level of a prediction data object that can be tolerated by the natural language processing and machine learning platform/system. For example, if the data prediction threshold is a positive value, and the prediction confidence score is lower than the data prediction threshold, the processing element determines that the prediction confidence score does not satisfy the data prediction threshold. If the data prediction threshold is a positive value, and the prediction confidence score is higher than the data prediction threshold, the processing element determines that the prediction confidence score satisfies the data prediction threshold.

Additionally, or alternatively, if the data prediction threshold is a negative value, and the prediction confidence score is lower than the data prediction threshold, the processing element determines that the prediction confidence score satisfies the data prediction threshold. If the data prediction threshold is a negative value, and the prediction confidence score is higher than the data prediction threshold, the processing element determines that the prediction confidence score does not satisfy the data prediction threshold.

Referring back to FIG. 13, if, at step/operation 1313, the processing element determines that the prediction confidence score satisfies the data prediction threshold, the example method 1300 proceeds to step/operation 1315. At step/operation 1315, a computing entity (such as the data object computing entity 105 described above in connection with FIG. 1 and FIG. 2) may include means (such as the processing element 205 of the data object computing entity 105 described above in connection with FIG. 2) to generate at least one recommendation data object.

In some embodiments, the processing element may generate at least one recommendation data object based at least in part on the at least one prediction data object in response to determining that the at least one prediction confidence score satisfies the data prediction threshold. In such embodiments, the prediction confidence score satisfying the data prediction threshold indicates that the prediction data object is generated with a sufficient confidence level as required by the natural language processing and machine learning platform/system.

For example, the at least one recommendation data object may indicate a recommended action in response to the preauthorization request based at least in part on the prediction data object calculated at step/operation 1311. For example, if the prediction data object indicates a high likelihood (satisfying a predetermined threshold) that there is at least one edge connecting the procedure node to the patient entity node and that there is at least one edge connecting the procedure node and the healthcare provider entity node, the processing element may generate the recommendation data object indicating a recommended action to approve the preauthorization request. If the prediction data object indicates a low likelihood (not satisfying a predetermined threshold) that there is at least one edge connecting the procedure node to the patient entity node and/or that there is at least one edge connecting the procedure node and the healthcare provider entity node, the processing element may generate the recommendation data object indicating a recommended action to deny the preauthorization request.

Other examples of recommended actions include automatically scheduling a medical appointment during a particular period. For example, in some embodiments, the recommendation data object may indicate that a corresponding patient identifier has a condition that requires seeking medical attention during the particular period. As a result, a computing entity may use the recommendation data object in order to automatically generate a medical appointment for the patient identifier during the particular period.

Other examples of recommended actions include automatically generating a prescription request for a particular medication. For example, in some embodiments, the recommendation data object may indicate that a corresponding patient identifier has a condition that requires using the particular medication. As a result, a computing entity may use the recommendation data object in order to automatically generate the corresponding prescription for the particular medication.

Other examples of recommended actions include automatically generating a hospital staff allocation arrangement and transmitting notifications to staff members in accordance with the hospital staff allocation arrangement. In some embodiments, the hospital staff allocation arrangement is determined based at least in part on optimizing a hospital staff allocation equation using a set of optimization operations. Examples of notifications include notifications to staff members about attending shifts or about not attending shifts.

Referring back to FIG. 13, if, at step/operation 1313, the processing element determines that the prediction confidence score does not satisfy the data prediction threshold, the example method 1300 proceeds to step/operation 1317. At step/operation 1317, a computing entity (such as the data object computing entity 105 described above in connection with FIG. 1 and FIG. 2) may include means (such as the processing element 205 of the data object computing entity 105 described above in connection with FIG. 2) to transmit a data prediction review request.

In some embodiments, the processing element may transmit a data prediction review request to the client computing device in response to determining that the at least one prediction confidence score does not satisfy the data prediction threshold. In such embodiments, the prediction confidence score not satisfying the data prediction threshold indicates that the prediction data object is generated with an insufficient confidence level that does not satisfy the requirements by the natural language processing and machine learning platform/system.

For example, the data prediction review request comprises an electronic request to manually review the preauthorization request and/or the prediction data object. In some embodiments, the responses to the data prediction review request may be recorded and provided to train the data prediction machine learning model.

Referring back to FIG. 13, subsequent to step/operation 1315 and/or step/operation 1317, the example method 1300 proceeds to step/operation 1319 and ends.

Thus, various embodiments of the present invention improve computational efficiency of machine learning models. Data that comprises unformatted natural language (such as that found in contracts) does not yield very accurate predictions in machine learning environments at least due to their unformatted structure. In particular, machine learning models in many machine learning environments require that the input data to be formatted in such as a way that can be easily ingested by the machine learning models, and data that comprises unformatted natural language fails to meet this requirement and causes decline in the accuracy of outputs (such as predictions) generated by machine learning models. Accuracy of output of machine learning models is imperative in the many contexts, including, but not limited to, healthcare context. Various embodiments of the present disclosure overcome such technical limitations and deficiencies. For example, various embodiments of the present disclosure define a graph-based format for data that would improve the accuracy of predictions and/or decision determinations by machine learning models based at least in part on natural language documents (such as, but not limited to, contracts, medical records and/or others).

V. Conclusion

Many modifications and other embodiments of the disclosure set forth herein will come to mind to one skilled in the art to which this disclosure pertains having the benefit of the teachings presented in the foregoing descriptions and the associated drawings. Therefore, it is to be understood that the disclosure is not to be limited to the specific embodiments disclosed and that modifications and other embodiments are intended to be included within the scope of the appended claims. Although specific terms are employed herein, they are used in a generic and descriptive sense only and not for purposes of limitation.

The invention claimed is:

1. A computing system comprising one or more processors and memory including program code, the memory and the program code configured to, with the one or more processors, cause the computing system to:
   retrieve a plurality of natural language data objects from a database;
   determine, based at least in part on the plurality of natural language data objects and by utilizing an entity extraction machine learning model, a plurality of entity identifiers for the plurality of natural language data objects, wherein: (i) the entity extraction machine learning model comprises an encoder sub-model and an entity classification sub-model, (ii) the encoder sub-model is configured to generate a plurality of text embeddings based at least in part on the plurality of natural language data objects, (iii) the entity classification sub-model is configured to determine an entity classification for each text embedding, and (iv) the plurality of entity identifiers are determined based at least in part on each entity classification;

determine, based at least in part on the plurality of entity identifiers and by utilizing the entity extraction machine learning model, one or more entity relationship identifiers for the plurality of natural language data objects, wherein: (i) the entity extraction machine learning model comprises an entity relationship classification sub-model, (ii) the entity relationship classification sub-model is configured to determine an entity relationship classification for each entity pair from the plurality of entity identifiers based at least in part on a subset of the plurality of text embeddings that corresponds to the entity pair, and (iii) the one or more entity relationship identifiers are determined based at least in part on each entity relationship classification;

generate, based at least in part on the plurality of entity identifiers and the one or more entity relationship identifiers, a graph-based data object that encodes the plurality of natural language data objects in accordance with a set of input formatting requirements for a data prediction machine learning model; and initiate the performance of the data prediction machine learning model to generate at least one prediction data object based at least in part on the graph-based data object.

2. The computing system of claim 1, wherein the encoder sub-model is associated with a multi-headed attention mechanism.

3. The computing system of claim 2, wherein the encoder sub-model comprises a Bidirectional Encoder Representations from Transformers (BERT) model.

4. The computing system of claim 2, wherein the program code is further configured to, with the one or more processors, cause the computing system to:

generate a plurality of nodes of the graph-based data object based at least in part on the plurality of entity identifiers; and generate a plurality of edges of the graph-based data object based at least in part on the one or more entity relationship identifiers.

5. The computing system of claim 4, wherein the plurality of natural language data objects comprises at least one textual contract data object and at least one medical record data object.

6. The computing system of claim 5, wherein the program code is further configured to, with the one or more processors, cause the computing system to:

in response to determining that the at least one textual contract data object and the at least one medical record data object are associated with a first patient entity identifier of the plurality of entity identifiers, generate a patient entity node;

generate, based at least in part on the at least one medical record data object, at least one symptom node and a first edge connecting the at least one symptom node to the patient entity node; and generate, based at least in part on the at least one textual contract data object, at least one procedure node and a second edge connecting the at least one procedure node to the patient entity node.

7. The computing system of claim 6, wherein the at least one procedure node is associated with at least one International Classification of Diseases (ICD) code.

8. The computing system of claim 1, wherein the graph-based data object comprises a plurality of nodes and a plurality of edges connecting the plurality of nodes, wherein each of the plurality of nodes corresponds to an entity associated with the plurality of natural language data objects, and wherein each of the plurality of edges corresponds to a relationship between entities associated with the plurality of natural language data objects.

9. The computing system of claim 8, wherein the plurality of nodes is associated with a plurality of node types, and wherein the plurality of edges is associated with a plurality of edge types that is determined based at least in part on the plurality of node types.

10. The computing system of claim 1, wherein the program code is further configured to, with the one or more processors, cause the computing system to:

receive, from a client computing device, a data prediction request associated with at least one entity identifier of the plurality of entity identifiers;

in response to receiving the data prediction request, identify, based at least in part on the at least one entity identifier, a related sub-graph of the graph-based data object that corresponds to the at least one entity identifier;

generate, based at least in part on the related sub-graph, the at least one prediction data object using the data prediction machine learning model; and transmit the at least one prediction data object to the client computing device.

11. The computing system of claim 10, wherein the program code is further configured to, with the one or more processors, cause the computing system to:

determine at least a first node from a plurality of nodes of the graph-based data object that is associated with the at least one entity identifier; and determine at least a first edge from a plurality of edges of the graph-based data object that connects the first node to at least a second node.

12. The computing system of claim 11, wherein the program code is further configured to, with the one or more processors, cause the computing system to:

generate the at least one prediction data object based at least in part on the first node, the first edge, and the second node using the data prediction machine learning model.

13. The computing system of claim 10, wherein the program code is further configured to, with the one or more processors, cause the computing system to:

train the data prediction machine learning model using a training data set, wherein the training data set comprises a plurality of historical data prediction requests that corresponds to a plurality of historical response data objects; and subsequent to training the data prediction machine learning model, generate the at least one prediction data object based at least in part on the data prediction request and the graph-based data object.

14. The computing system of claim 10, wherein the data prediction request is associated with a preauthorization request and comprises a procedure identifier, a patient entity identifier, and a healthcare provider entity identifier.

15. The computing system of claim 14, wherein the program code is further configured to, with the one or more processors, cause the computing system to:

identify, from a plurality of nodes of the graph-based data object, a patient entity node associated with the patient entity identifier;

identify, from the plurality of nodes of the graph-based data object, a healthcare provider entity node associated with the healthcare provider entity identifier;

identify, from the plurality of nodes of the graph-based data object, a procedure node associated with the procedure identifier; and calculate, based at least in part on the data prediction machine learning model, (i) a prediction data object that indicates a predicted probability of at least one edge connecting the procedure node to the patient entity node and to the healthcare provider entity node and (ii) a prediction confidence score associated with the prediction data object, wherein the data prediction machine learning model is an unsupervised machine learning model.

16. The computing system of claim 15, wherein the program code is further configured to, with the one or more processors, cause the computing system to:

determine whether the prediction confidence score satisfies a data prediction threshold.

17. The computing system of claim 16, wherein the program code is further configured to, with the one or more processors, cause the computing system to:

in response to determining that the prediction confidence score satisfies the data prediction threshold, generate at least one recommendation data object based at least in part on the at least one prediction data object.

18. The computing system of claim 16, wherein the program code is further configured to, with the one or more processors, cause the computing system to:

in response to determining that the prediction confidence score does not satisfy the data prediction threshold, transmit a data prediction review request to the client computing device.

19. A computer-implemented method comprising:

retrieving, using one or more processors, a plurality of natural language data objects from a database;

determining, using the one or more processors and based at least in part on the plurality of natural language data objects and by utilizing an entity extraction machine learning model, a plurality of entity identifiers for the plurality of natural language data objects, wherein: (i) the entity extraction machine learning model comprises an encoder sub-model and an entity classification sub-model, (ii) the encoder sub-model is configured to generate a plurality of text embeddings based at least in part on the plurality of natural language data objects, (iii) the entity classification sub-model is configured to determine an entity classification for each text embedding, and (iv) the plurality of entity identifiers are determined based at least in part on each entity classification;

determining, using the one or more processors and based at least in part on the plurality of entity identifiers and by utilizing the entity extraction machine learning model, one or more entity relationship identifiers for the plurality of natural language data objects, wherein: (i) the entity extraction machine learning model comprises an entity relationship classification sub-model, (ii) the entity relationship classification sub-model is configured to determine an entity relationship classification for each entity pair from the plurality of entity identifiers based at least in part on a subset of the plurality of text embeddings that corresponds to the entity pair, and (iii) the one or more entity relationship identifiers are determined based at least in part on each entity relationship classification;

generating, using the one or more processors and based at least in part on the plurality of entity identifiers and the one or more entity relationship identifiers, a graph-based data object that encodes the plurality of natural language data objects in accordance with a set of input formatting requirements for a data prediction machine learning model; and initiating, using the one or more processors, the performance of the data prediction machine learning model to generate at least one prediction data object based actions based at least in part on the graph-based data object.

20. One or more non-transitory computer-readable storage media including instructions that, when executed by one or more processors, cause the one or more processors to:

retrieve a plurality of natural language data objects from a database;

determine, based at least in part on the plurality of natural language data objects and by utilizing an entity extraction machine learning model, a plurality of entity identifiers for the plurality of natural language data objects, wherein: (i) the entity extraction machine learning model comprises an encoder sub-model and an entity classification sub-model, (ii) the encoder sub-model is configured to generate a plurality of text embeddings based at least in part on the plurality of natural language data objects, (iii) the entity classification sub-model is configured to determine an entity classification for each text embedding, and (iv) the plurality of entity identifiers are determined based at least in part on each entity classification;

determine, based at least in part on the plurality of entity identifiers and by utilizing the entity extraction machine learning model, one or more entity relationship identifiers for the plurality of natural language data objects, wherein: (i) the entity extraction machine learning model comprises an entity relationship classification sub-model, (ii) the entity relationship classification sub-model is configured to determine an entity relationship classification for each entity pair from the plurality of entity identifiers based at least in part on a subset of the plurality of text embeddings that corresponds to the entity pair, and (iii) the one or more entity relationship identifiers are determined based at least in part on each entity relationship classification;

generate, based at least in part on the plurality of entity identifiers and the one or more entity relationship identifiers, a graph-based data object that encodes the plurality of natural language data objects in accordance with a set of input formatting requirements for a data prediction machine learning model; and initiate the performance of the data prediction machine learning model to generate at least one prediction data object based at least in part on the graph-based data object.

* * * * *

UNITED STATES PATENT AND TRADEMARK OFFICE
CERTIFICATE OF CORRECTION

| | | |
|---|---|---|
| PATENT NO. | : 12,087,413 B2 | Page 1 of 1 |
| APPLICATION NO. | : 17/448292 | |
| DATED | : September 10, 2024 | |
| INVENTOR(S) | : Irfan Bulu | |

It is certified that error appears in the above-identified patent and that said Letters Patent is hereby corrected as shown below:

In the Claims

In Column 52, Line 17, Claim 19, delete "actions based at least" and insert -- at least --, therefor.

Signed and Sealed this
Twenty-second Day of April, 2025

Coke Morgan Stewart
*Acting Director of the United States Patent and Trademark Office*